(12) United States Patent
Fadli

(10) Patent No.: US 9,078,828 B2
(45) Date of Patent: Jul. 14, 2015

(54) CATIONIC TETRAHYDROPYRAZOLOPYRIDINES, DYE COMPOSITION COMPRISING SUCH OXIDATION BASES, IMPLEMENTATION PROCESS THEREFOR AND USE THEREOF

(71) Applicant: L'OREAL, Paris (FR)

(72) Inventor: Aziz Fadli, Chelles (FR)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 14/365,710

(22) PCT Filed: Dec. 17, 2012

(86) PCT No.: PCT/EP2012/075817
§ 371 (c)(1),
(2) Date: Jun. 16, 2014

(87) PCT Pub. No.: WO2013/087933
PCT Pub. Date: Jun. 20, 2013

(65) Prior Publication Data
US 2014/0352715 A1    Dec. 4, 2014

Related U.S. Application Data

(60) Provisional application No. 61/593,448, filed on Feb. 1, 2012.

(30) Foreign Application Priority Data

Dec. 16, 2011    (FR) ..................... 11 61841

(51) Int. Cl.
*A61Q 5/10*    (2006.01)
*A61K 8/49*    (2006.01)
*C07D 471/04*    (2006.01)

(52) U.S. Cl.
CPC . *A61K 8/494* (2013.01); *A61K 8/49* (2013.01); *A61K 8/4946* (2013.01); *A61K 8/4953* (2013.01); *A61Q 5/10* (2013.01); *C07D 471/04* (2013.01); *A61K 2800/88* (2013.01)

(58) Field of Classification Search
CPC ......... A61Q 5/10; A61K 8/4953; A61K 8/49; A61K 8/494; A61K 8/4946
USPC .................................................. 8/405, 690
See application file for complete search history.

(56) References Cited

U.S. PATENT DOCUMENTS

| 4,003,699 A | 1/1977 | Rose et al. |
| RE30,199 E | 1/1980 | Rose et al. |
| 4,823,985 A | 4/1989 | Grollier et al. |
| 5,061,289 A | 10/1991 | Clausen et al. |
| 5,380,340 A | 1/1995 | Neunhoeffer et al. |
| 5,534,267 A | 7/1996 | Neunhoeffer et al. |
| 5,663,366 A | 9/1997 | Neunhoeffer et al. |
| 5,766,576 A | 6/1998 | Lowe et al. |
| 6,099,592 A | 8/2000 | Vidal et al. |
| 6,099,593 A | 8/2000 | Terranova et al. |
| 6,284,003 B1 | 9/2001 | Rose et al. |
| 6,338,741 B1 | 1/2002 | Vidal et al. |
| 6,645,258 B2 | 11/2003 | Vidal et al. |
| 7,578,855 B2 * | 8/2009 | Fadli ................... 8/405 |
| 2002/0050013 A1 | 5/2002 | Vidal et al. |
| 2003/0019051 A9 | 1/2003 | Vidal et al. |
| 2007/0136959 A1 | 6/2007 | Fadli |

FOREIGN PATENT DOCUMENTS

| DE | 2359399 A1 | 6/1975 |
| DE | 3843892 A1 | 6/1990 |
| DE | 4133957 A1 | 4/1993 |
| DE | 19543988 A1 | 5/1997 |
| EP | 0770375 A1 | 5/1997 |
| FR | 2586913 A1 | 3/1987 |
| FR | 2733749 | 11/1996 |
| FR | 2750048 | 12/1997 |
| FR | 2893027 A1 | 5/2007 |
| GB | 1026978 | 4/1966 |
| GB | 1153196 | 5/1969 |
| JP | 02019576 | 1/1990 |
| JP | 5163124 | 6/1993 |
| WO | 9408969 A1 | 4/1994 |
| WO | 9408970 A1 | 4/1994 |
| WO | 9615765 A1 | 5/1996 |

OTHER PUBLICATIONS

STIC Search REport dated Oct. 2, 2014.*
International Search Report for PCT/EP2012/075817, May 2013.
English language abstract for EP 0770375A1, Mar. 1997.
English language abstract for JP 02019576A, Jan. 1990.
English language abstract for JP 05163124A, Jun. 1993.

* cited by examiner

*Primary Examiner* — Eisa Elhilo
(74) *Attorney, Agent, or Firm* — The Marbury Law Group, PLLC

(57) ABSTRACT

The present invention relates to particular cationic tetrahydropyrazolopyridine compounds of formula (I) below and also to the use thereof for dyeing keratin fibers, in particular human keratin fibers such as the hair. The invention also relates to a dye composition comprising, in a suitable dyeing medium, one or more cationic tetrahydropyrazolopyridines as defined previously. Finally, the invention relates to a dyeing device using the said composition.

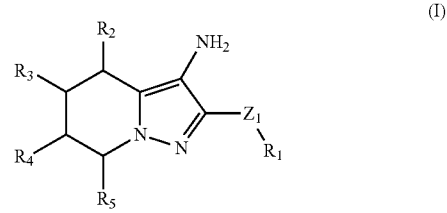

(I)

15 Claims, No Drawings

CATIONIC TETRAHYDROPYRAZOLOPYRIDINES, DYE COMPOSITION COMPRISING SUCH OXIDATION BASES, IMPLEMENTATION PROCESS THEREFOR AND USE THEREOF

CROSS REFERENCE TO RELATED APPLICATIONS

This is a national stage application of PCT/EP2012/075817, filed internationally on Dec. 17, 2012, which claims priority to U.S. Provisional Application No. 61/593,448, filed on Feb. 1, 2012, as well as French Application FR 1161841, filed Dec. 16, 2011, all of which are incorporated herein by their entireties.

The present invention relates to particular cationic tetrahydropyrazolopyridine compounds and also to the use thereof for dyeing keratin fibres, in particular human keratin fibres such as the hair.

The invention also relates to a composition for dyeing keratin fibres comprising such cationic tetrahydropyrazolopyridine compounds in a suitable dyeing medium, and also to a dyeing process and a multi-compartment device using the said composition.

The present invention relates to the field of dyeing keratin fibres and more particularly to the field of hair dyeing.

It is known practice to dye keratin fibres, and in particular human hair, with dye compositions containing oxidation dye precursors, which are generally known as oxidation bases, such as ortho- or para-phenylenediamines, ortho- or para-aminophenols and heterocyclic compounds. These oxidation bases are colourless or weakly coloured compounds, which, when combined with oxidizing products, are able to produce coloured compounds by a process of oxidative condensation.

It is also known that the shades obtained with oxidation bases can be varied by combining them with couplers or coloration modifiers, the latter being selected more particularly from aromatic meta-diaminobenzenes, meta-aminophenols, meta-diphenols and certain heterocyclic compounds such as indole compounds.

The variety of molecules used as oxidation bases and couplers allows a wide range of colours to be obtained.

The "permanent" coloration obtained by means of these oxidation dyes must moreover satisfy a certain number of requirements. Thus, it must have no toxicological drawbacks, it must allow shades to be obtained in the desired strength, and it must show good fastness with respect to external agents such as light, bad weather, washing, permanent-waving, perspiration and rubbing.

The dyes must also allow grey hair to be covered, and they must be as unselective as possible, i.e. they must make it possible to produce the smallest possible coloration differences along the same lock of keratin fibre, which is generally differently sensitized (i.e. damaged) between its end and its root.

It is also known practice to use oxidation bases of the para-phenylenediamine, para-toluenediamine or para-aminophenol type for dyeing keratin fibres, especially the hair.

However, these oxidation bases generally have the drawback of giving colorations that are not sufficiently strong, chromatic or fast with respect to external agents and/or that are too selective. Furthermore, these oxidation bases have unfavourable harmlessness.

There is thus a real need for oxidation bases that have improved dyeing properties, especially in terms of strength, chromaticity, colour buildup, selectivity and/or resistance with respect to external agents, and that are also capable of leading to a wider range of colours, while at the same time improving the harmlessness of the oxidation bases used in oxidation dyeing.

These aims are achieved with the present invention, one subject of which is especially cationic tetrahydropyrazolopyridines of formula (I), optical isomers and geometrical isomers thereof, addition salts thereof and/or solvates thereof:

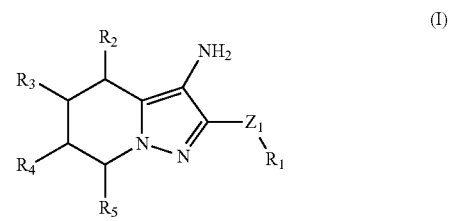

in which formula (I):

$R_2$, $R_3$, $R_4$ and $R_5$ represent, independently of each other, a hydrogen atom; a halogen atom; a linear or branched $C_1$-$C_4$ alkyl radical; a linear or branched $C_1$-$C_4$ hydroxyalkyl radical;

$R_2$ and $R_3$, $R_3$ and $R_4$ or $R_4$ and $R_5$ may form, together with the carbon atoms to which they are attached, a saturated, unsaturated or aromatic 5- to 8-membered ring optionally substituted with one or more radicals chosen from hydroxyl, alkoxy, $C_1$-$C_4$ alkyl and $C_1$-$C_4$ hydroxyalkyl radicals;

$Z_1$ represents an oxygen atom or a group $NR_6$;

$R_6$ represents a hydrogen atom or a linear or branched $C_1$-$C_4$ alkyl radical;

$R_1$ represents:
  a linear or branched $C_1$-$C_{20}$ alkyl radical, substituted and/or interrupted with a cationic radical, the said alkyl radical being optionally interrupted with one or more oxygen atoms and/or with one or more groups NR6, optionally substituted with one or more radicals chosen from hydroxyl and $C_1$-$C_4$ alkoxy or hydroxyalkyl radicals;
  a saturated, unsaturated or aromatic, 5- to 8-membered ring or heterocycle substituted with a cationic radical and optionally substituted with one or more radicals chosen from hydroxyl and $C_1$-$C_4$ alkoxy or hydroxyalkyl radicals;

when $Z_1$ represents a group $NR_6$ then:
  $R_1$ and $R_6$ may form, together with the nitrogen atom to which they are attached, a saturated, unsaturated, aromatic or non-aromatic, 5- to 8-membered mono- or polycationic, preferably monocationic, heterocycle, optionally substituted with one or more radicals chosen from $C_1$-$C_4$ alkyl, hydroxyl, $C_1$-$C_4$ alkoxyamino, $(C_1$-$C_4)$alkylamino, $(C_1$-$C_4)$dialkylamino, thio SH, $(C_1$-$C_4)$alkylthio, carboxyl, C(O)OH or C(O)O$^-$, M$^+$ with M$^+$, which may be present or absent depending on the cationic charge number of the compound (I), representing an alkali metal, alkaline-earth metal or ammonium; $(C_1$-$C_4)$alkylcarbonyl; sulfonyl —S(O)n-R, —S(O)$_p$—O—R, —O—S(O)$_p$—R with R representing a hydrogen atom or a $C_1$-$C_4$ (hydroxy)alkyl group, n=0, 1 or 2, p=1 or 2, amido —C(O)—NRR' or —N(R)—C(O)—R', —N(R)—C(O)—NRR' with R and R', which may be identical or different, representing a hydrogen atom or a $C_1$-$C_4$ (hydroxy)alkyl group, $C_1$-$C_4$ hydroxyalkyls, this heterocycle possibly containing one or more heteroatoms chosen from N and O, preferably N, $R_1$ and $R_6$ may form, together with the nitrogen atom to which they are attached, a saturated or unsaturated, 5- to 8-membered noncationic heterocycle optionally substituted with one or more radicals chosen from $C_1$-$C_{10}$ alkyl; hydroxyl OH; $C_1$-$C_4$ alkoxy; amino; ($C_1$-$C_4$)alkylamino; ($C_1$-$C_4$)dialkylamino; thio SH, ($C_1$-$C_4$)alkylthio, carboxyl, C(O)OH or C(O)O$^-$, M$^+$ with M$^+$, which may be present or absent depending on the cationic charge number of the compound (I), representing an alkali metal, alkaline-earth metal or ammonium; ($C_1$-$C_4$)alkylcarbonyl; sulfonyl —S(O)n-R, —S(O)$_p$—O—R, —O—S(O)$_p$—R with R representing a hydrogen atom or a $C_1$-$C_4$ (hydroxy)alkyl group, n=0, 1 or 2, p=1 or 2, amido —C(O)—NRR' or —N(R)—C(O)—R', —N(R)—C(O)—NRR' with R and R', which may be identical or different, representing a hydrogen atom or a $C_1$-$C_4$ (hydroxy)alkyl group, $C_1$-$C_4$ hydroxyalkyls.

The invention also relates to the use of one or more cationic tetrahydropyrazolopyridines of formula (I) as defined previously, as oxidation bases for dyeing keratin fibres, in particular human keratin fibres such as the hair.

The present invention also relates to a composition for dyeing keratin fibres, in particular human keratin fibres such as the hair, comprising, in a suitable dyeing medium, one or more cationic tetrahydropyrazolopyridines of formula (I) as defined previously.

In particular, the invention also relates to the use of the said composition for dyeing keratin fibres, in particular human keratin fibres such as the hair.

The invention also relates to a process for dyeing keratin fibres, in particular human keratin fibres such as the hair, in which the said dye composition according to the invention is applied to the said fibres in the presence of one or more oxidizing agents for a time that is sufficient to obtain the desired coloration, after which the resulting fibres are rinsed, optionally washed with shampoo, rinsed again and dried or left to dry.

Another subject of the present invention concerns a multi-compartment device or dyeing kit comprising a first compartment containing a dye composition as described above and a second compartment containing one or more oxidizing agents.

The multi-compartment device is thus suitable for performing the dyeing process according to the invention.

The cationic tetrahydropyrazolopyridines according to the invention thus make it possible to obtain improved dyeing of keratin fibres, especially in terms of strength or chromaticity, and/or of selectivity and/or of resistance to external agents such as shampoos, sweat, light and permanent reshaping.

The cationic tetrahydropyrazolopyridines according to the invention also make it possible to achieve a wide range of colours, while at the same time improving the harmlessness of the oxidation bases used in oxidation dyeing.

Furthermore, the cationic tetrahydropyrazolopyridine compounds according to the invention show good solubility and allow satisfactory colour buildup.

For the purposes of the present invention, the term "buildup" of the colour of keratin fibres means the variation in coloration between locks of undyed grey hair and locks of dyed hair.

Other characteristics, aspects, subjects and advantages of the present invention will emerge even more clearly on reading the description and the examples that follow.

I. Cationic Tetrahydropyrazolopyridine Compounds

The cationic tetrahydropyrazolopyridine compounds of formula (I) as defined previously comprise a cationic charge by virtue of the presence of a cationic radical in their structure.

In the context of the invention, the expression "cationic radical present in the compound of formula (I)" means any linear or branched or heterocyclic radical comprising a quaternary ammonium, this quaternary ammonium being of the type —N$^+$R$_a$R$_b$R$_c$, R$_a$, R$_b$ and R$_c$, which may be identical or different, representing a $C_1$-$C_6$ alkyl radical which may be substituted with a hydroxyl. Ra and R$_b$ may together form a 5- to 8-membered heterocycle, the radical R$_c$ then being a $C_1$-$C_6$ alkyl radical which may be substituted with a hydroxyl radical.

Preferably, R$_a$, R$_b$ and R$_c$, which may be identical or different, represent a $C_1$-$C_2$ alkyl radical, in particular methyl, optionally substituted with a hydroxyl radical.

Preferably, when R$_a$ and R$_b$ together form a 5- to 8-membered heterocycle, the radical R$_c$ then represents a $C_1$-$C_2$ alkyl radical which may be substituted with a hydroxyl radical.

Thus, the tetrahydropyrazolopyridines of formula (I) according to the invention bear a permanent cationic charge that is independent of the pH of the medium in which the compounds are formulated.

Examples of cationic radicals that may be mentioned include trimethylammonium, triethylammonium, dimethylethylammonium, diethylmethylammonium, diisopropylmethylammonium, diethylpropylammonium, hydroxyethyldiethylammonium, di-β-hydroxyethylmethylammonium and tri-β-hydroxyethylammonium radicals.

The term "cationic heterocycle" means a 5- to 8-membered heterocycle in which at least one of the chain members is a quaternary ammonium as defined previously.

In particular, the cationic heterocycle is a 5- to 8-membered heterocycle in which at least one of the chain members is a quaternary ammonium as defined previously.

Examples of cationic heterocycles that may be mentioned include imidazoliums, pyridiniums, piperaziniums, pyrrolidiniums, morpholiniums, pyrimidiniums, thiazoliums, benzimidazoliums, benzothiazoliums, oxazoliums, benzotriazoliums, pyrazoliums, for example pyrrolidine, piperidine, morpholine and piperazine rings, triazoliums and benzoxazoliums.

These cationic heterocycles are optionally substituted with one or more identical or different radicals chosen from ($C_1$-$C_4$)alkyl and ($C_1$-$C_4$)hydroxyalkyl radicals.

Preferably, the cationic radicals are chosen from trimethylammonium, triethylammonium, dimethylethylammonium, diethylmethylammonium, diisopropylmethylammonium, hydroxyethyldiethylammonium, imidazoliums, pyridiniums, piperaziniums, pyrrolidiniums, morpholiniums, pyrimidiniums, thiazoliums and benzimidazoliums.

More preferentially, the cationic radicals are chosen from trimethylammonium radicals and cationic heterocycles, especially imidazolium, piperazinium, pyrrolidinium, piperidinium and morpholinium.

Even more preferentially, the cationic radicals are chosen from trimethylammonium and pyrrolidinium radicals, especially trimethylammonium.

The term "saturated or unsaturated 5- to 8-membered noncationic heterocycle" means a 5- to 8-membered ring in which at least one of the ring members is a heteroatom chosen from O, N and S, for instance imidazole or pyrimidine.

Preferably, when $R_1$ represents a linear or branched $C_1$-$C_{20}$ alkyl radical, then the said radical is substituted with a cationic radical.

According to one preferred embodiment, in formula (I), are such that, taken together or separately:

- $R_2$, $R_3$, $R_4$ and $R_5$ represent, independently of each other, a hydrogen atom or a linear or branched $C_1$-$C_4$ alkyl radical, preferably a hydrogen atom or a linear $C_1$-$C_4$ alkyl radical and even more preferentially a hydrogen atom or a methyl radical,
- $R_2$ and $R_3$, $R_3$ and $R_4$ or $R_4$ and $R_5$ may form, together with the carbon atoms that bear them, a saturated, unsaturated or aromatic 5- to 8-membered and preferably 5- or 6-membered ring, and preferably an unsubstituted 5- or 6-membered carbon-based ring, and more preferentially $R_4$ and $R_5$ may form, together with the carbon atoms that bear them, an unsubstituted 5- or 6-membered carbon-based ring;
- $Z_1$ represents an oxygen atom or a group $NR_6$;
- $R_6$ represents a hydrogen atom or a linear or branched $C_1$-$C_2$ alkyl radical;
- $R_1$ represents a linear or branched $C_1$-$C_8$ alkyl radical, substituted with a cationic radical, optionally substituted with one or more radicals chosen from $C_1$-$C_4$ alkyl and $C_1$-$C_4$ alkoxy radicals, or

- $R_1$ represents a saturated, unsaturated or aromatic, 5- to 8-membered non-cationic ring or heterocycle, substituted with a cationic radical, when $Z_1$ represents $NR_6$ then:

- $R_1$ and $R_6$ may form, together with the nitrogen atom to which they are attached, a saturated or unsaturated cationic 5- to 8-membered heterocycle optionally substituted with one or more radicals chosen from $C_1$-$C_{10}$ alkyl, hydroxyl, $C_1$-$C_4$ alkoxy, amino, ($C_1$-$C_4$) alkylamino, di($C_1$-$C_4$)alkylamino, ($C_1$-$C_4$)alkylcarbonyl, amido and $C_1$-$C_4$ hydroxyalkyl radicals, it being possible for this heterocycle to contain one or more heteroatoms chosen from N or O, preferably N, or

- $R_1$ and $R_6$ may form, together with the nitrogen atom to which they are attached, a saturated or unsaturated non-cationic 5- to 8-membered heterocycle substituted with a cationic radical and optionally substituted with one or more radicals chosen from C1-C10 alkyl, hydroxyl, C1-C4 alkoxy, amino, (C1-C4)alkylamino, di(C1-C4)alkylamino, (C1-C4)alkylcarbonyl, amido and C1-C4 hydroxyalkyl radicals.

Preferably, $R_2$ and $R_3$, on the one hand, represent a hydrogen atom and $R_4$ and $R_5$, on the other hand, represent a hydrogen atom or a $C_1$-$C_4$ alkyl radical, especially methyl.

More preferentially, $R_2$, $R_3$, $R_4$ and $R_5$ represent a hydrogen atom.

Preferably, $Z_1$ represents a group $NR_6$ with $R_6$ possibly being a hydrogen atom.

According to a first preferred variant of the invention, $R_2$, $R_3$, $R_4$ and $R_5$ represent a hydrogen atom, $Z_1$ represents a group NH and $R_1$ represents a saturated linear $C_2$-$C_8$ alkyl radical, optionally interrupted with a heteroatom such as oxygen or a group NH, $R_1$ being substituted with a cationic radical chosen from trimethylammonium radicals and imidazolium, piperazinium, pyrrolidinium, piperidinium or morpholinium cationic heterocycles.

In accordance with this first variant, $R_1$ is substituted with a trimethylammonium radical.

According to a second preferred variant of the invention, $R_2$, $R_3$, $R_4$ and $R_5$ represent a hydrogen atom, $Z_1$ represents a group $N_6$ and $R^1$ and $R_6$ form, together with the nitrogen atom to which they are attached, a saturated, 5- to 8-membered non-cationic heterocycle, substituted with a cationic radical preferably chosen from trimethylammonium, diethylmethylammonium, imidazolium, piperazinium, piperidinium, pyrrolidinium and morpholinium radicals.

In accordance with this second variant and even more preferentially, the non-cationic heterocycle is chosen from pyrrolidine, piperidine and morpholine, this ring being substituted with a cationic radical chosen from trimethylammonium and diethylmethylammonium radicals.

In accordance with this variant and even more preferentially, the non-cationic heterocycle is chosen from pyrrolidine, piperidine and morpholine, this ring being substituted with a cationic radical chosen from trimethylammonium and diethylmethylammonium radicals.

According to a third preferred variant of the invention, $R_2$, $R_3$, $R_4$ and $R_5$ represent a hydrogen atom, $Z_1$ represents a group $NR_6$ and $R_1$ and $R_6$ form, together with the nitrogen atom to which they are attached, a cationic heterocycle chosen from piperazinium, imidazolium, pyrrolidinium, piperidinium and morpholinium substituted with one or more identical or different radicals chosen from $C_1$-$C_4$ hydroxyalkyl and $C_1$-$C_4$ alkyl, preferentially a piperazinium radical substituted with one or more identical or different radicals chosen from $C_1$-$C_4$ hydroxyalkyl and $C_1$-$C_4$ alkyl.

According to one embodiment, Z represents an oxygen atom.

According to another embodiment, Z represents a group $NR_6$, in which $R_1$ and $R_6$ form, together with the nitrogen atom to which they are attached, a saturated or unsaturated, 5- to 8-membered cationic heterocycle, optionally substituted with one or more radicals chosen from $C_1$-$C_4$ alkyl and $C_1$-$C_4$ hydroxyalkyl radicals, this heterocycle containing a nitrogen atom other than that belonging to the group $NR_6$.

In the context of the invention, a derivative of formula (I) is understood to encompass all mesomeric or isomeric forms.

The electrical neutrality of the compounds of formula (I) is ensured by an organic or mineral, cosmetically acceptable anion or mixture of anions, noted An⁻.

An– denotes, for example, a halide such as chloride, bromide, fluoride or iodide; a hydroxide; a sulfate; a hydrogen sulfate; an alkyl sulfate in which the linear or branched alkyl part is of $C_1$-$C_6$, such as the methyl sulfate or ethyl sulfate ion; a carbonate; a hydrogen carbonate; a salt of a carboxylic acid, such as formate, acetate, citrate, tartrate or oxalate; an alkylsulfonate for which the linear or branched alkyl part is of $C_1$-$C_6$, such as the methylsulfonate ion; an arylsulfonate for which the aryl part, preferably phenyl, is optionally substituted with one or more C1-C4 alkyl radicals, for instance 4-tolylsulfonate; an alkylsulfonate such as mesylate.

The compounds of general formula (I) may be in free form or in the form of salts, such as addition salts with an inorganic acid preferably chosen from hydrochloric acid, hydrobromic acid, sulfuric acid and phosphoric acid or with an organic acid such as, for example, citric acid, succinic acid, tartaric acid, lactic acid, 4-toluoylsulfonic acid, benzenesulfonic acid, acetic acid, para-toluenesulfonic acid, formic acid and methanesulfonic acid.

For the purposes of the present invention, the cationic charge originating from the acid salt of compound (I) is not considered as a cationic radical borne by $Z_1$.

The compounds of general formula (I) may also be in the form of solvates, for example in the form of a hydrate or of a solvate of a linear or branched $C_1$-$C_6$ alcohol such as ethanol or isopropanol.

Preferably, the cationic tetrahydropyrazolopyridines of formula (I) according to the invention are chosen from the following compounds and mixtures thereof, and also the geometrical or optical isomer forms thereof, the organic or mineral acid salts thereof or the solvates thereof such as hydrates:

Compound 1

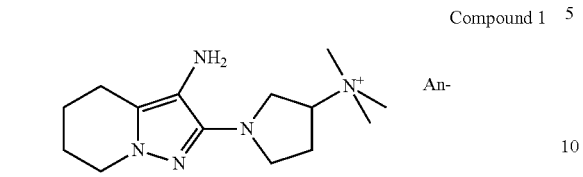

1-(3-amino-4,5,6,7-tetrahydropyrazolo[1,5-a]pyridin-2-yl)-N,N,N-trimethylpyrrolidin-3-aminium, An⁻

Compound 2

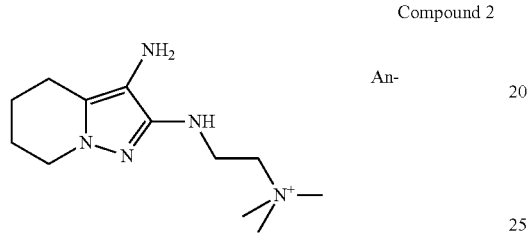

2-[(3-amino-4,5,6,7-tetrahydropyrazolo[1,5-a]pyridin-2-yl)amino]-N,N,N-trimethylethanaminium, An⁻

Compound 3

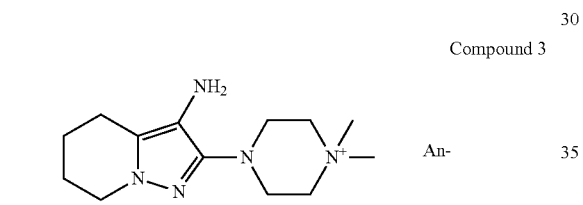

1-(3-amino-4,5,6,7-tetrahydropyrazolo[1,5-a]pyridin-2-yl)-N,N,N-trimethylpyrrolidin-3-aminium, An⁻

Compound 4

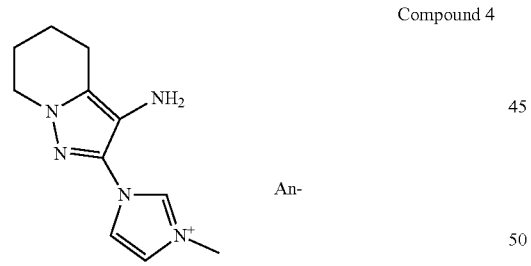

1-(3-amino-4,5,6,7-tetrahydropyrazolo[1,5-a]pyridin-2-yl)-3-methyl-1H-imidazol-3-ium, An⁻

Compound 5

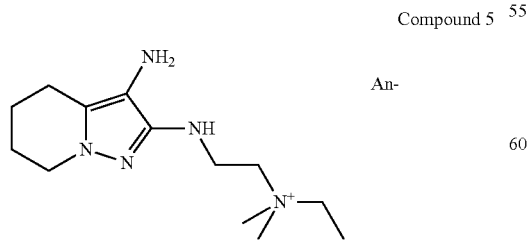

2-[(3-amino-4,5,6,7-tetrahydropyrazolo[1,5-a]pyridin-2-yl)amino]-N-ethyl-N,N-dimethylethanaminium, An⁻

Compound 6

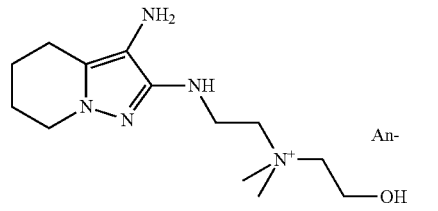

2-[(3-amino-4,5,6,7-tetrahydropyrazolo[1,5-a]pyridin-2-yl)amino]-N-(2-hydroxyethyl)-N,N-dimethylethanaminium, An⁻

Compound 7

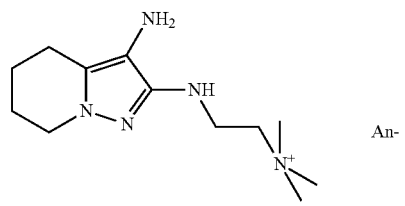

3-[(3-amino-4,5,6,7-tetrahydropyrazolo[1,5-a]pyridin-2-yl)amino]-N,N,N-trimethylpropan-1-aminium, An⁻

Compound 8

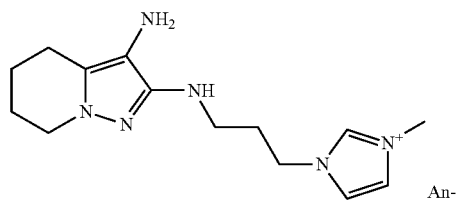

1-{3-[(3-amino-4,5,6,7-tetrahydropyrazolo[1,5-a]pyridin-2-yl)amino]propyl}-3-methyl-1H-imidazol-3-ium, An⁻

Compound 9

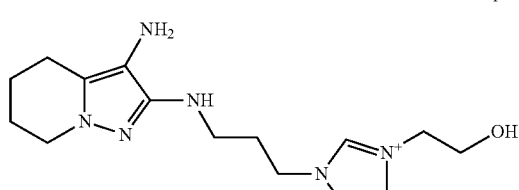

1-{3-[(3-amino-4,5,6,7-tetrahydropyrazolo[1,5-a]pyridin-2-yl)amino]propyl}-3-(2-hydroxyethyl)-1H-imidazol-3-ium, An⁻

Compound 10

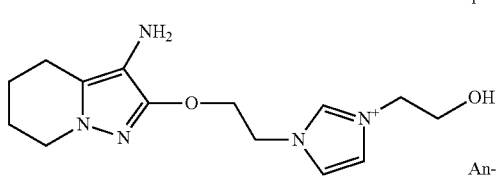

1-{3-[(3-amino-4,5,6,7-tetrahydropyrazolo[1,5-a]pyridin-2-yl)amino]propyl}-3-(2-hydroxyethyl)-1H-imidazol-3-ium, An⁻

-continued

Compound 11

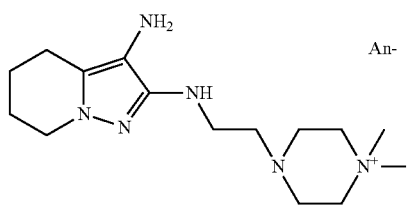

4-{2-[(3-amino-4,5,6,7-tetrahydropyrazolo[1,5-a]pyridin-2-yl)amino]ethyl}-1,1-dimethylpiperazin-1-ium, An⁻

Compound 12

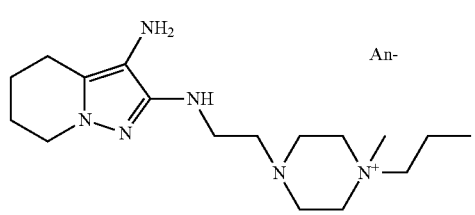

4-{2-[(3-amino-4,5,6,7-tetrahydropyrazolo[1,5-a]pyridin-2-yl)amino]ethyl}-1-methyl-1-propylpiperazin-1-ium, An⁻

Compound 13

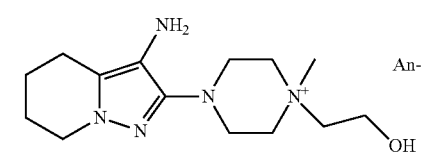

4-(3-amino-4,5,6,7-tetrahydropyrazolo[1,5-a]pyridin-2-yl)-1-(2-hydroxyethyl)-1-methylpiperazin-1-ium, An⁻

Compound 14

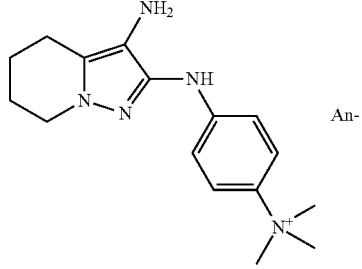

4-[(3-amino-4,5,6,7-tetrahydropyrazolo[1,5-a]pyridin-2-yl)-amino]-N,N,N-trimethylanilinium, An⁻

Compound 15

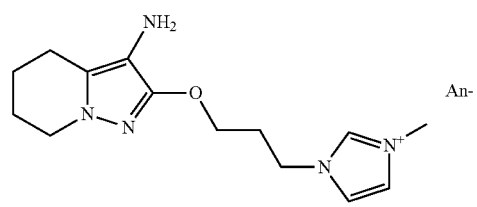

1-{3-[(3-amino-4,5,6,7-tetrahydropyrazolo[1,5-a]pyridin-2-yl)oxy]propyl}-3-methyl-1H-imidazol-3-ium, An⁻

Compound 16

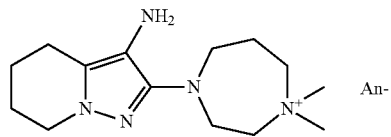

4-(3-amino-4,5,6,7-tetrahydropyrazolo[1,5-a]pyridin-2-yl)-1,1-dimethyl-1,4-diazepan-1-ium An⁻

Compound 17

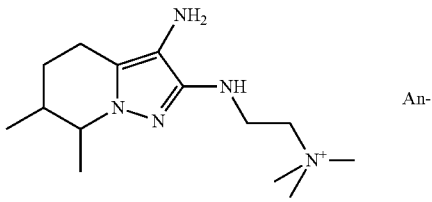

2-[(3-amino-6,7-dimethyl-4,5-dihydropyrazolo[1,5-a]pyridin-2-yl)amino]-N,N,N-trimethylethanaminium, An⁻

Compound 18

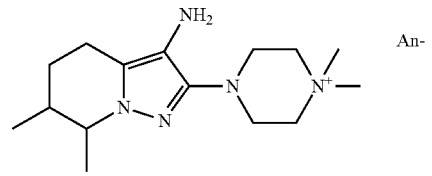

4-(3-amino-6,7-dimethyl-4,5,6,7-tetrahydropyrazolo[1,5-a]pyridin-2-yl)-1,1-dimethylpiperazin-1-ium, An⁻

Compound 19

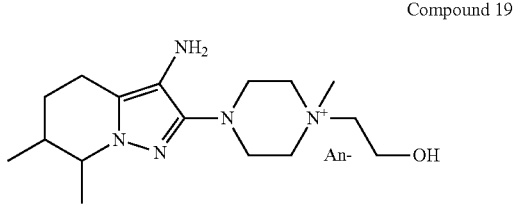

4-(3-amino-6,7-dimethyl-4,5,6,7-tetrahydropyrazolo[1,5-a]pyridin-2-yl)-1-(2-hydroxyethyl)-1-methylpiperazin-1-ium, An⁻

Compound 20

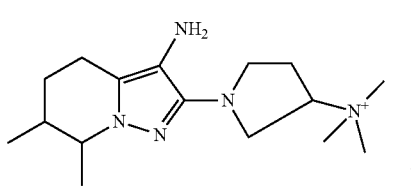

1-(3-amino-6,7-dimethyl-4,5,6,7-tetrahydropyrazolo[1,5-a]pyridin-2-yl)-N,N,N-trimethylpyrrolidin-3-aminium, An⁻

Compound 21

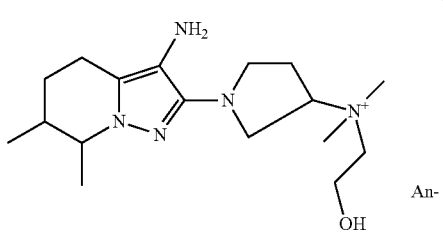

4,5,6,7-tetrahydropyrazolo[1,5-a]pyridin-2-yl)-N-(2-hydroxyethyl)-N,N-dimethylpyrrolidin-3-aminium, An⁻

Compound 22

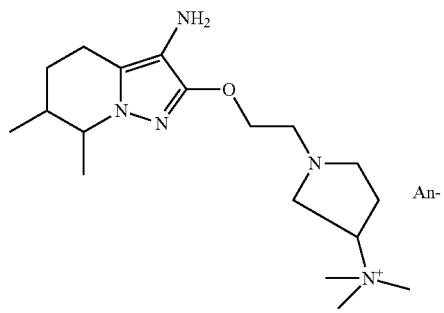

1-{2-[(3-amino-6,7-dimethyl-4,5,6,7-tetrahydropyrazolo[1,5-a]pyridin-2-yl)oxy]ethyl}-N,N,N-trimethylpyrrolidin-3-aminium, An⁻

Compound 23

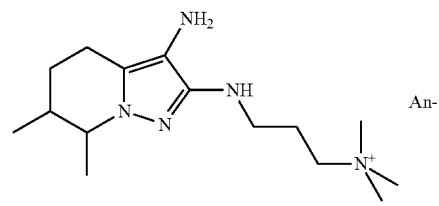

3-[(3-amino-6,7-dimethyl-4,5,6,7-tetrahydropyrazolo[1,5-a]pyridin-2-yl)amino]-N,N,N-trimethylpropan-1-aminium, An⁻

Compound 24

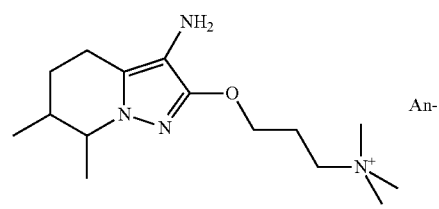

3-[(3-amino-6,7-dimethyl-4,5,6,7-tetrahydropyrazolo[1,5-a]pyridin-2-yl)oxy]-N,N,N-trimethylpropan-1-aminium, An⁻

Compound 25

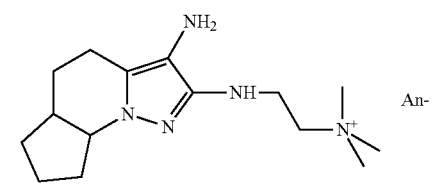

2-[(3-amino-6,7,8,8a-tetrahydro-5aH-cyclopenta[e]pyrazolo[1,5-a]pyridin-2-yl)amino]-N,N,N-trimethylethanaminium, An⁻

Compound 26

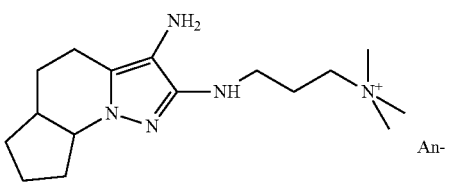

3-[(3-amino-5,5a,6,7,8,8a-hexahydro-4H-cyclopenta[e]pyrazolo[1,5-a]pyridin-2-yl)amino]-N,N,N-trimethylpropan-1-aminium, An⁻

Compound 27

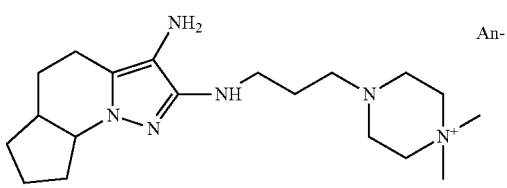

4-{3-[(3-amino-5,5a,6,7,8,8a-hexahydro-4H-cyclopenta[e]pyrazolo[1,5-a]pyridin-2-yl)amino]propyl}-1,1-dimethylpiperazin-1-ium, An⁻

Compound 28

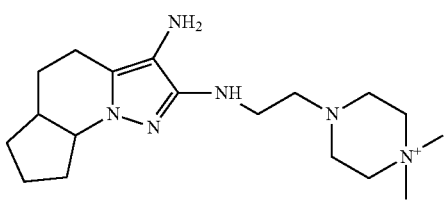

4-{2-[(3-amino-5,5a,6,7,8,8a-hexahydro-4H-cyclopenta[e]pyrazolo[1,5-a]pyridin-2-yl)amino]ethyl}-1,1-dimethylpiperazin-1-ium, An⁻

Compound 29

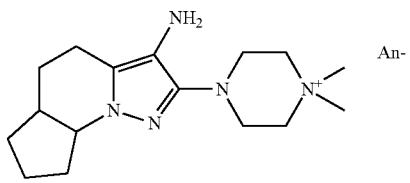

4-[(3-amino-5,5a,6,7,8,8a-hexahydro-4H-cyclopenta[e]pyrazolo[1,5-a]pyridin-2-yl)-1,1-dimethylpiperazin-1-ium, An⁻

Compound 30

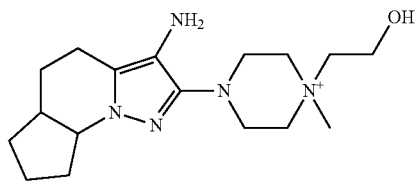

4-[(3-amino-5,5a,6,7,8,8a-hexahydro-4H-cyclopenta[e]pyrazolo[1,5-a]pyridin-2-yl)-1-(2-hydroxyethyl)-1-methylpiperazin-1-ium, An⁻

Compound 31

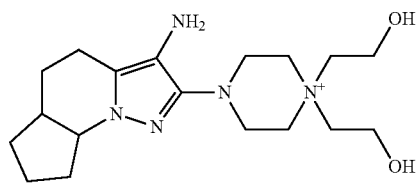

4-[(3-amino-5,5a,6,7,8,8a-hexahydro-4H-cyclopenta[e]pyrazolo[1,5-a]pyridin-2-yl)-1,1-bis(2-hydroxyethyl)piperazin-1-ium, An⁻

-continued

Compound 32

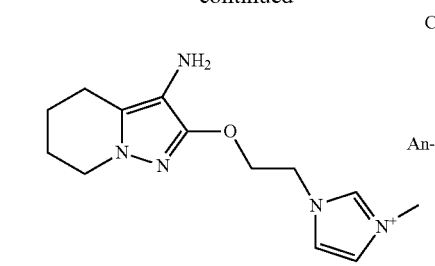

1-{2-[(3-amino-4,5,6,7-tetrahydropyrazolo[1,5-a]pyridin-2-yl)oxy]ethyl}-3-methyl-1H-imidazol-3-ium, An⁻

Compound 33

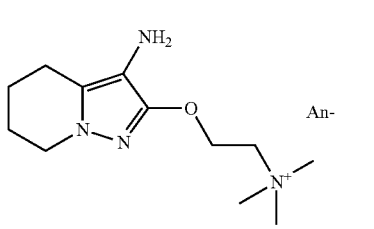

2-[(3-amino-4,5,6,7-tetrahydropyrazolo[1,5-a]pyridin-2-yl)oxy]-N,N,N-trimethylethanaminium, An⁻

Compound 34

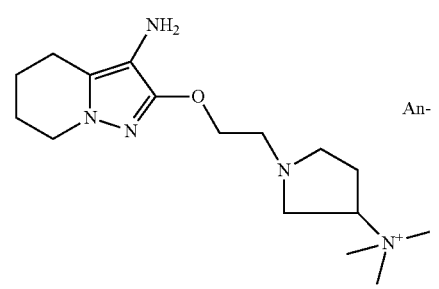

1-{2-[(3-amino-4,5,6,7-tetrahydropyrazolo[1,5-a]pyridin-2-yl)oxy]ethyl}-N,N,N-trimethylpyrrolidin-3-aminium, An⁻

Compound 35

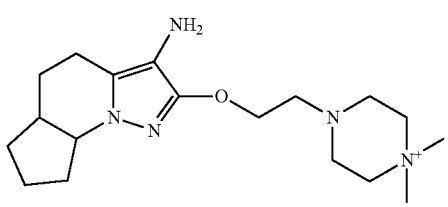

4-{2-[(3-amino-5,5a,6,7,8,8a-hexahydro-4H-cyclopenta[e]pyrazolo[1,5-a]pyridin-2-yl)oxy]ethyl}-1,1-dimethylpiperazin-1-ium, An⁻

Preferably, the cationic tetrahydropyrazolopyridines according to the invention are chosen from compounds 1, 2 and 3, and also mixtures thereof.

An– has the same meaning as indicated previously.

II. Synthetic Process

The present invention also relates to a process for synthesizing a cationic tetrahydropyrazolopyridine of general formula (I) as defined above starting with compounds (A), (B), (C) and (D) according to the following scheme:

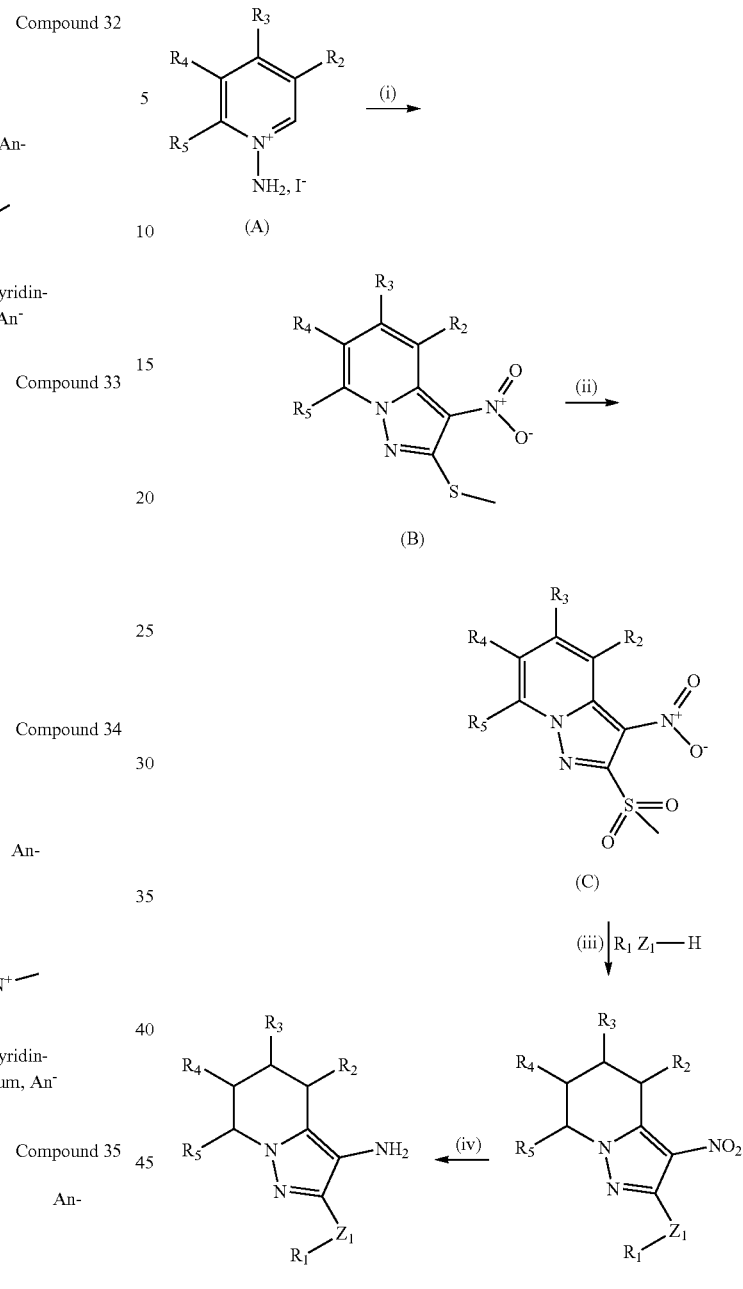

in which $R_1$, $Z_1$, $R_2$, $R_3$, $R_4$ and $R_5$ have the same meanings as those indicated in formula (I), and in which:

in a step (i), an N-aminopyridinium derivative of formula (A) is reacted with at least two equivalents of 1,1-bis(methylthio)-2-nitroethylene, preferably in a polar solvent, to obtain a 2-methylsulfanyl-3-nitropyrazolo[1,5-a]pyridine derivative of formula (B), in a step (ii), an oxidation reaction is performed on the sulfur atom in position 2 of the compound of formula (B) to obtain the sulfonyl derivative thereof of formula (C), in a step (iii), the compound of formula (C) is reacted with a nucleophilic compound of formula $R_1Z_1H$ or $R_1Z_1{-}$, $M^+$ with $M^+$ representing an alkali metal or an alkaline-earth metal such as Li, Na or K, in order to replace the group —S(O)$_2$—CH$_3$ with a group —Z$_1$R$_1$ in order to obtain the compound of formula (D), and in a step (iv), one or more reduction reactions are performed in a polar solvent on the compound of formula (D) to give a cationic tetrahydropyrazolopyridine of formula (I).

Step (i) for obtaining the compound of formula (B) from the N-aminopyridinium derivative of formula (A) may be performed under the conditions described in the publication entitled Heterocycle, Vol. 6, No. 4, 1977.

Depending on the nature of the groups R1 in the compound of formula (D), it is possible to perform one or more reduction reactions. These reductions may be performed sequentially, i.e. by first reducing the nitro function to an amino function, and then reducing the pyridine ring.

The reduction of the nitro group of these compounds is performed under standard conditions, for example by performing a hydrogenation reaction under heterogeneous catalysis in the presence of Pd/C, Pd(II)/C, Ni/Ra, etc., or alternatively by performing a reduction reaction with a metal, for example with zinc, iron, tin, etc. (see *Advanced Organic Chemistry*, 3rd Edition, J. March, 1985, Wiley Interscience and *Reduction in Organic Chemistry*, M. Hudlicky, 1983, Ellis Horwood Series Chemical Science).

According to one particular embodiment, the cationic tetrahydropyrazolopyridine compounds of general formula (I), in which Z$_1$ corresponds to an oxygen atom and R$_1$ corresponds to a C$_2$ alkyl radical substituted with a cationic trimethylammonium radical, may be obtained according to the following reaction scheme:

in which R$_1$, Z$_1$, R$_2$, R$_3$, R$_4$ and R$_5$ have the same meanings as those indicated in formula (I) and R'$_1$ represents a C$_2$ alkyl radical substituted with a group —NR$_7$R$_8$, R$_7$ and R$_8$, which may be identical or different, representing a C$_1$-C$_6$ alkyl radical which may be substituted with a hydroxyl, and in which:

steps (i), (ii) and (iv) are identical to those described previously, and in a step (iii)1, the compound of formula (C) is reacted with a compound of formula R'$_1$Z$_1$H or R'$_1$Z$_1^-$, M$^+$ with M$^+$ representing an alkali metal or an alkaline-earth metal such as Li, Na or K, in order to replace the group —S(O)$_2$—CH$_3$ with a group —Z1R'1 such as R$_7$R$_8$N(CH$_2$)$_2$OH or an alkoxide R$_7$R$_8$N(CH$_2$)$_2$O$^-$M$^+$ with M$^+$ as defined previously, to obtain the compound of formula (D1), and then, in a step (iii)2, an alkylation step is performed on the compound of formula (D1) to obtain a compound of formula (D'1).

According to another embodiment, the cationic tetrahydropyrazolopyridine compounds of general formula (I), in which Z$_1$ corresponds to an oxygen atom and R$_1$ corresponds to a C$_2$ alkyl radical substituted with a cationic trimethylammonium radical, may also be obtained according to the following reaction scheme:

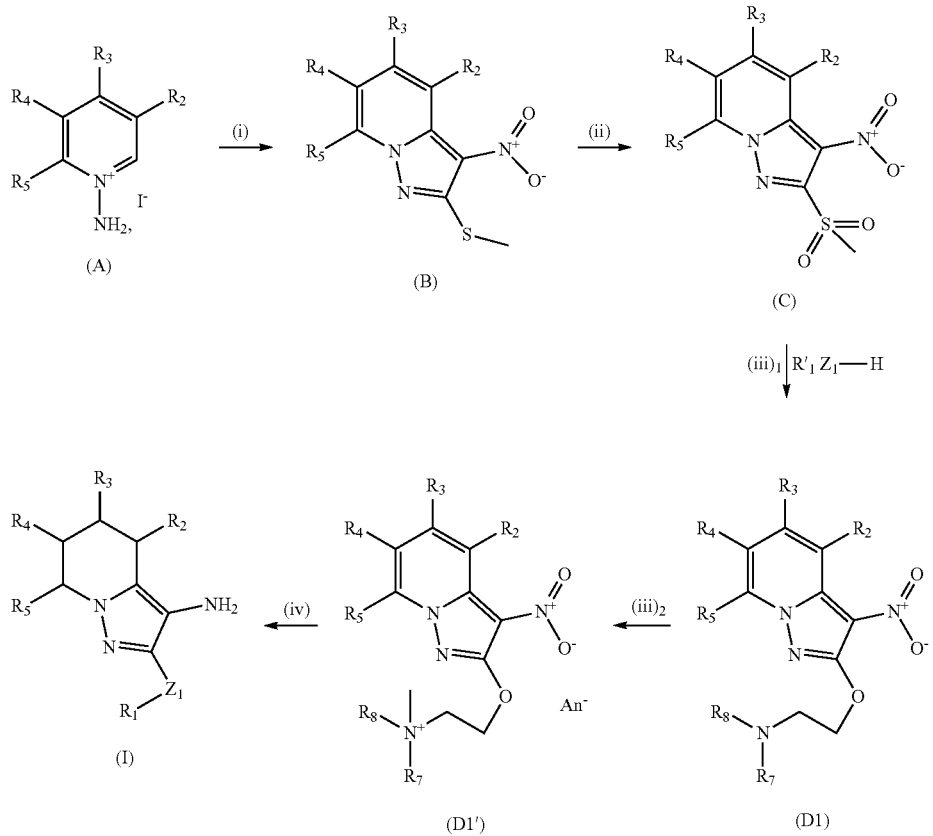

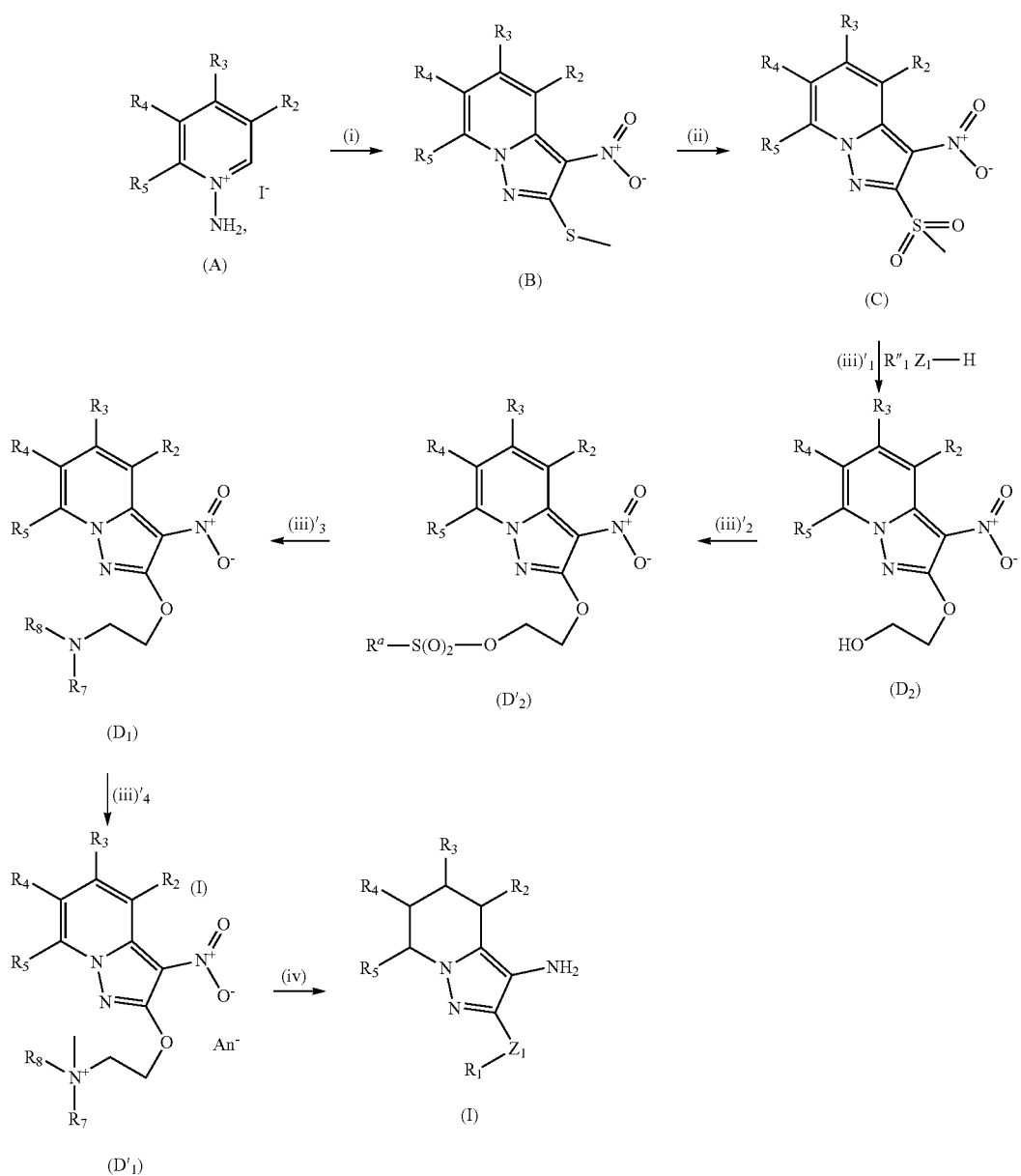

in which $R_1$, $Z_1$, $R_2$, $R_3$, $R_4$ and $R_5$ have the same meanings as those indicated in formula (I) and $R''_1$ represents a $C_2$ alkyl radical substituted with a hydroxyl group, and in which:

- steps (i), (ii) and (iv) are identical to those described previously, and
- in a step (iii)'1, the compound of formula (C) is reacted with a nucleophilic compound of formula $R''_1Z_1H$ or $R''_1Z_1^-$, $M^+$ with M+ representing an alkali metal or an alkaline-earth metal such as Li, Na or K, in order to replace the group —S(O)$_2$—CH$_3$ with a group —Z$_1$R''$_1$ such as 1,2-dihydroxyethane, in order to obtain the compound of formula (D2), and then
- in a step (iii)'2, a substitution step is performed on the hydroxyl group with a (C1-C6)alkylsulfonyl, arylsulfonyl or benzylsulfonyl Ra—S(O)2-O—, especially with a halide compound such as the mesyl or tosyl halide, to obtain the compound of formula (D'2) comprising a nucleofugal leaving group Ra—S(O)2-O with Ra representing a group (C$_1$-C$_6$)alkyl, aryl or benzyl;
- in a step (iii)'3, a substitution step is performed on the group Ra—S(O)$_2$— with an amine group to obtain the compound of formula (D1), followed by performing a reaction directed towards rendering the compound of formula (D1) cationic, or "cationization", in order to obtain the compound of formula (D'1).

In particular, the substitution reaction (iii)"1 is performed in a dipolar solvent such as acetonitrile, tetrahydrofuran (THF) or in dimethylformamide (DMF) or N-methylpyrrolidone (NMP), or in an alcohol such as ethanol, in the presence of a base such as triethylamine, ethyldiisopropylamine, sodium hydroxide or potassium hydroxide, for example, and one or more equivalents of $R''_1Z_1H$ for 1 to 24 hours at a temperature from 20° C. to the reflux temperature of the solvent.

The hydroxyl function thus introduced is then replaced with a halide in order to introduce a leaving group (for example a mesyl or tosyl halide) in a solvent such as acetonitrile, tetrahydrofuran (THF) or in an alcohol such as ethanol, for example, in the presence of a base such as triethylamine, ethyldiisopropylamine, sodium hydroxide or potassium hydroxide, for example, for 1 to 24 hours at a temperature from 20° C. to the reflux temperature of the solvent.

The substitution of the leaving group introduced during the preceding step is carried out by reaction with an amine or an alcohol.

The cationization is performed by reaction with at least one equivalent of an alkyl or aryl halide, methyl sulfate or an alkyl carbonate in a solvent such as tetrahydrofuran (THF), acetonitrile, dioxane or ethyl acetate for 15 minutes to 24 hours at a temperature ranging from 15° C. to the reflux temperature of the solvent, to give the cationic nitro compounds.

Thus, step (iii) defined in the synthetic process may be performed in several steps.

A subject of the present invention is also the compounds of formula (D) as defined in the synthetic schemes mentioned above and in which $R_1$, $Z_1$, $R_2$, $R_3$, $R_4$ and $R_5$ have the same meanings as those indicated in formula (I) of the cationic tetrahydropyrazolopyridine compounds.

Preferably, the compounds of formula (D) are chosen from the compounds that lead to the cationic tetrahydropyrazolopyridine compounds 1 to 35 mentioned previously.

Preferentially, the compounds of formula (D) are chosen from the compounds that lead to the cationic tetrahydropyrazolopyridine compounds 1, 2 and 3.

The invention also relates to the use of one or more cationic tetrahydropyrazolopyridine compounds of formula (I) as defined previously, in the presence of one or more oxidizing agents, for dyeing keratin fibres, in particular human keratin fibres such as the hair.

III. Dye Composition

The present invention also relates to a composition for dyeing keratin fibres, in particular human keratin fibres such as the hair, comprising, in a suitable dyeing medium, one or more cationic tetrahydropyrazolopyridine compounds of formula (I) as defined above.

Preferably, the dye composition comprises one or more cationic tetrahydropyrazolopyridine compounds of formula (I) chosen from compounds 1 to 35, and mixtures thereof.

More preferentially, the dye composition comprises one or more cationic tetrahydropyrazolopyridine compounds of formula (I) chosen from compounds 1, 2 and 3, and mixtures thereof.

The cationic tetrahydropyrazolopyridines as defined previously may be present in the composition according to the invention in a content ranging from 1% to 20% by weight and preferably in a content ranging from 1% to 5% by weight relative to the total weight of the dye composition.

The dye composition according to the invention may contain and preferably contains one or more couplers that are conventionally used for dyeing keratin fibres. Among these couplers, mention may be made especially of meta-phenylenediamines, meta-aminophenols, meta-diphenols, naphthalene couplers and heterocyclic couplers, and the addition salts thereof.

Examples of couplers that may be mentioned include 2-methyl-5-aminophenol, 5-N-(β-hydroxyethyl)amino-2-methylphenol, 6-chloro-2-methyl-5-aminophenol, 3-aminophenol, 2,4-dichloro-3-aminophenol, 5-amino-4-chloro-o-cresol, 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, 3-ureidoaniline, 3-ureido-1-dimethylaminobenzene, sesamol, 1-β-hydroxyethylamino-3,4-methylenedioxybenzene, α-naphthol, 2-methyl-1-naphthol, 1,5-dihydroxynaphthalene, 2,7-naphthalenediol, 1-acetoxy-2-methylnaphthalene, 6-hydroxyindole, 4-hydroxyindole, 4-hydroxy-N-methylindole, 2-amino-3-hydroxypyridine, 6-hydroxybenzomorpholine, 3,5-diamino-2,6-dimethoxypyridine, 2,6-dihydroxy-3-4-dimethylpyridine, 3-amino-2-methylamino-6-methoxypyridine, 1-N-(β-hydroxyethyl)amino-3,4-methylenedioxybenzene, 2,6-bis(β-hydroxyethylamino)toluene and 3-methyl-1-phenyl-5-pyrazolone and the addition salts thereof with an acid.

In the dye composition of the present invention, the coupler(s), if they are present, generally represent an amount of between 0.001% and 10% by weight approximately relative to the total weight of the composition, and preferably between 0.005% and 6% by weight relative to the total weight of the composition.

The dye composition of the invention may optionally comprise one or more additional oxidation bases conventionally used for the dyeing of keratin fibres, other than the compounds of formula (I).

By way of example, these additional oxidation bases are chosen from para-phenylenediamines other than the bases of formula (I), bis(phenyl)alkylenediamines, para-aminophenols, bis-para-aminophenols, ortho-aminophenols and heterocyclic bases, and the addition salts thereof.

Among the para-phenylenediamines, examples that may be mentioned include para-phenylenediamine, para-toluenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis(β-hydroxyethyl)amino-2-chloroaniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N-ethyl-N-(β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine, 4-aminophenylpyrrolidine, 2-thienyl-para-phenylenediamine, 2-β-hydroxyethylamino-5-aminotoluene and 3-hydroxy-1-(4'-aminophenyl)pyrrolidine, and the addition salts thereof with an acid.

Among the para-phenylenediamines mentioned above, para-phenylenediamine, para-toluenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine and 2-β-acetylaminoethyloxy-para-phenylenediamine, and the addition salts thereof with an acid, are particularly preferred.

Among the bis(phenyl)alkylenediamines, examples that may be mentioned include N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl)ethylenediamine and 1,8-bis(2,5-diaminophenoxy)-3,6-dioxaoctane, and the addition salts thereof with an acid.

Among the para-aminophenols, examples that may be mentioned include para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol, 4-amino-2-fluorophenol, 1-hydroxy-4-methylaminobenzene and 2,2'-methylenebis(4-aminophenol), and the addition salts thereof with an acid.

Among the ortho-aminophenols, examples that may be mentioned include 2-aminophenol, 2-amino-5-methylphenol, 2-amino-6-methylphenol and 5-acetamido-2-aminophenol, and the addition salts thereof with an acid.

Mention may be made, among heterocyclic bases, by way of example, of pyridine derivatives, pyrimidine derivatives and pyrazole derivatives.

Among the pyridine derivatives, mention may be made of the compounds described, for example, in patents GB 1 026 978 and GB 153 196, for instance 2,5-diaminopyridine, 2-(4-methoxyphenyl)amino-3-aminopyridine, 2,3-diamino-6-methoxypyridine, 2-(β-methoxyethyl)amino-3-amino-6-methoxypyridine and 3,4-diaminopyridine, and the addition salts thereof with an acid.

Among the pyrimidine derivatives, mention may be made of the compounds described, for example, in patents DE 2359399; JP 63-169571; JP 05-163124; EP 0 770375 or patent application WO 96/15765, for instance 2,4,5,6-tetraminopyrimidine, 4-hydroxy-2,5,6-triamino pyrimidine, 2-hydroxy-4,5,6-triaminopyrimidine, 2,4-dihydroxy-5,6-diaminopyrimidine and 2,5,6-triaminopyrimidine, and pyrazolopyrimidine derivatives such as those mentioned in patent application FR-A-2 750 048, and among which mention may be made of pyrazolo[1,5-a]pyrimidine-3,7-diamine, 2,5-dimethylpyrazolo[1,5-a]pyrimidine-3,7-diamine, pyrazolo[1,5-a]pyrimidine-3,5-diamine, 2,7-dimethylpyrazolo[1,5-a]pyrimidine-3,5-diamine, 3-aminopyrazolo[1,5-a]pyrimidin-7-ol, 3-aminopyrazolo[1,5-a]pyrimidin-5-ol, 2-(3-aminopyrazolo[1,5-a]pyrimidin-7-ylamino)ethanol, 2-(7-aminopyrazolo[1,5-a]pyrimidin-3-ylamino)ethanol, 2-[(3-aminopyrazolo[1,5-a]pyrimidin-7-yl)(2-hydroxyethyl)amino]ethanol, 2-[(7-aminopyrazolo[1,5-a]pyrimidin-3-yl)(2-hydroxyethyl)amino]ethanol, 5,6-dimethylpyrazolo[1,5-a]pyrimidine-3,7-diamine, 2,6-dimethylpyrazolo[1,5-a]pyrimidine-3,7-diamine, 2,5,N7,N7-tetramethylpyrazolo[1,5-a]pyrimidine-3,7-diamine and 3-amino-5-methyl-7-imidazolylpropylaminopyrazolo[1,5-a]pyrimidine, and the addition salts thereof with an acid, and the tautomeric forms thereof, when a tautomeric equilibrium exists.

Among the pyrazole derivatives that may be mentioned are the compounds described in the patents DE 3843892, DE 4133957 and patent applications WO 94/08969, WO 94/08970, FR-A-2 733 749 and DE 195 43 988, such as 4,5-diamino-1-methylpyrazole, 4,5-diamino-1-(β-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-methylaminopyrazole, 3,5-diamino-4-(β-hydroxyethyl)amino-1-methylpyrazole, and the addition salts thereof with an acid.

In general, the addition salts of the additional oxidation bases and of the couplers that can be used in the context of the invention are especially chosen from addition salts with an acid, such as hydrochlorides, hydrobromides, sulfates, citrates, succinates, tartrates, lactates, tosylates, benzenesulfonates, phosphates and acetates, and the addition salts with a base such as sodium hydroxide, potassium hydroxide, aqueous ammonia, amines or alkanolamines.

The dye composition in accordance with the invention may also contain one or more direct dyes that may in particular be chosen from nitrobenzene dyes, azo direct dyes and methine direct dyes. These direct dyes may be of nonionic, anionic or cationic nature.

The medium that is suitable for dyeing, also known as the dye support, generally comprises water or a mixture of water and of one or more organic solvents, for example C1-C4 lower alkanols such as ethanol and isopropanol, polyols, for instance propylene glycol, dipropylene glycol or glycerol, and polyols, for instance dipropylene glycol monomethyl ether.

The solvent(s) are generally present in proportions that may be between 1% and 40% by weight approximately and more preferably between 3% and 30% by weight approximately relative to the total weight of the dye composition.

The dye composition in accordance with the invention may also contain various adjuvants conventionally used in hair dye compositions, such as anionic, cationic, nonionic, amphoteric or zwitterionic surfactants or mixtures thereof, anionic, cationic, nonionic, amphoteric or zwitterionic polymers or mixtures thereof, inorganic or organic thickeners, and in particular anionic, cationic, nonionic and amphoteric polymeric associative thickeners, antioxidants, penetrants, sequestrants, fragrances, buffers, dispersants, conditioning agents, for instance volatile or non-volatile, modified or unmodified silicones, film-forming agents, ceramides, preserving agents and opacifiers.

The above adjuvants are generally present in an amount, for each of them, of between 0.01% and 20% by weight relative to the weight of the composition.

Needless to say, a person skilled in the art will take care to select this or these optional additional compound(s) such that the advantageous properties intrinsically associated with the oxidation dye composition in accordance with the invention are not, or are not substantially, adversely affected by the envisaged addition(s).

The pH of the dye composition in accordance with the invention is generally between 3 and 12 approximately and preferably between 5 and 11 approximately. It may be adjusted to the desired value by means of acidifying or basifying agents usually used in the dyeing of keratin fibres, or alternatively using standard buffer systems.

Among the acidifying agents, mention may be made, by way of example, of inorganic or organic acids, for instance hydrochloric acid, orthophosphoric acid, sulfuric acid, carboxylic acids, for instance acetic acid, tartaric acid, citric acid and lactic acid, and sulfonic acids.

Among the basifying agents that may be mentioned, for example, are aqueous ammonia, alkaline carbonates, alkanolamines such as monoethanolamine, diethanolamine and triethanolamine and derivatives thereof, sodium hydroxide, potassium hydroxide and the compounds of formula (II) below:

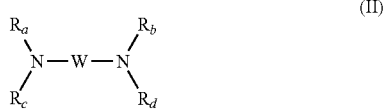

in which W is a propylene residue optionally substituted with a hydroxyl group or a C1-C4 alkyl radical; and Ra, Rb, Rc and Rd, which may be identical or different, represent a hydrogen atom or a C1-C4 alkyl or C1-C4 hydroxyalkyl radical.

The composition according to the invention may comprise one or more oxidizing agents.

The oxidizing agents are those conventionally used for the oxidation dyeing of keratin fibres, for example hydrogen peroxide, urea peroxide, alkali metal bromates, persalts such as perborates and persulfates, peracids and oxidase enzymes, among which mention may be made of peroxidases, 2-electron oxidoreductases such as uricases, and 4-electron oxygenases, for instance laccases. Hydrogen peroxide is particularly preferred.

The dye composition with or without oxidizing agent according to the invention may be in various forms, such as in the form of liquids, creams or gels, or in any other form that is suitable for dyeing keratin fibres, and especially human hair.

It may result from the mixing, at the time of use, of several compositions.

In particular, it results from the mixing of at least two compositions, one comprising one or more oxidation bases chosen from the compounds of formula (I) or addition salts thereof with an acid, optionally one or more additional oxidation bases other than the compounds of formula (I) or salts thereof, and optionally one or more couplers, and a second composition comprising one or more oxidizing agents as described previously.

In particular, the invention also relates to the use of a dye composition as defined previously for dyeing keratin fibres, in particular human keratin fibres such as the hair.

The present invention also relates to a process for dyeing keratin fibres, in particular human keratin fibres such as the hair, in which the said dye composition according to the invention is applied to the said fibres in the presence of one or more oxidizing agents for a time that is sufficient to obtain the desired coloration, after which the resulting fibres are rinsed, optionally washed with shampoo, rinsed again and dried or left to dry.

The colour may be revealed at acidic, neutral or alkaline pH and the oxidizing agent may be added to the composition of the invention just at the time of use, or it may be used starting with an oxidizing composition containing it, applied simultaneously or sequentially to the composition of the invention.

In one particular embodiment, the composition devoid of oxidizing agent according to the present invention is mixed, preferably at the time of use, with a composition containing, in a medium appropriate for dyeing, one or more oxidizing agents, these oxidizing agents being present in an amount sufficient to develop a colouring. The mixture obtained is then applied to the keratin fibres.

In accordance with this particular embodiment, a ready-to-use composition is obtained, which is a mixture of a composition according to the invention with one or more oxidizing agents.

After a leave-on time of from 3 to 50 minutes approximately and preferably 5 to 30 minutes approximately, the keratin fibres are rinsed, washed with shampoo, rinsed again and then dried.

The oxidizing agents are those indicated above.

The oxidizing composition may also contain various adjuvants conventionally used in compositions for dyeing the hair and as defined above.

The pH of the oxidizing composition containing the oxidizing agent is such that, after mixing with the dye composition, the pH of the resulting composition applied to the keratin fibres preferably varies between 3 and 12 approximately and more preferably still between 5 and 11. It may be adjusted to the desired value by means of acidifying or basifying agents usually used in the dyeing of keratin fibres and as defined above.

The ready-to-use composition which is ultimately applied to the keratin fibres may be in a variety of forms, such as in the form of liquids, creams or gels or any other form appropriate for carrying out dyeing of keratin fibres, and in particular of human hair.

Another subject of the invention is a dyeing "kit" or multi-compartment device in which a first compartment contains the dye composition devoid of oxidizing agent of the present invention defined above, comprising one or more oxidation bases chosen from the compound of formula (I) or the addition salts thereof with an acid, and a second compartment contains one or more oxidizing agents.

These devices may be equipped with a means for dispensing the desired mixture on the hair, such as the devices described in patent FR-2 586 913 in the name of the Applicant.

The examples that follow serve to illustrate the invention without, however, being limiting in nature.

EXAMPLES

Synthesis Examples

Example 1

Synthesis of 1-(3-amino-4,5,6,7-tetrahydropyrazolo[1,5-a]pyridin-2-yl)-N,N,N-trimethylpyrrolidin-3-aminium chloride hydrochloride

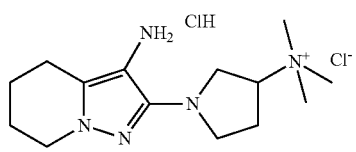 [SMILES: C[N+](C)(C)C1CCN(c2nn3c(c2N)CCCC3)C1 ; Cl ; [Cl-]]

Step 1: Synthesis of 2-methylsulfanyl-3-nitropyrazolo[1,5-a]pyridine

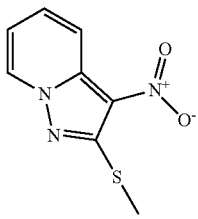

2-Methylsulfanyl-3-nitropyrazolo[1,5-a]pyridine

A solution of 111 g of 1-N-aminopyridinium (0.5 mol) in DMF (500 ml) is prepared in a 2-liter three-necked flask equipped with a mechanical stirrer and an internal temperature probe, and placed under a stream of nitrogen.

Potassium carbonate (207.3 g, 3 eq.) is then added in a single portion, followed by 1,1-bis(methylthio)-2-nitroethylene (165.2 g, 2 eq.), also in a single portion. The reaction medium sets to a solid. 500 ml of DMF are added in order to make the reaction medium more fluid.

After stirring for 48 hours at room temperature, the reaction medium is poured onto 4 liters of ice-water. The precipitate formed is filtered off and washed thoroughly with water (5 liters) and then dried at 80° C. under vacuum.

The solid thus obtained is freed of the excess 1,1-bis(methylthio)-2-nitroethylene (30 mol % determined by $^1$H-NMR) by reslurrying in ethyl acetate. After draining the product by suction and drying, 72 g of a beige-yellow solid corresponding to the expected product are obtained.

The NMR spectrum indicates that the product obtained corresponds to the expected product.

Step 2: Synthesis of 2-methanesulfonyl-3-nitropyrazolo[1,5-a]pyridine

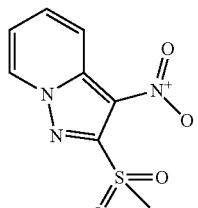

2-Methanesulfonyl-3-nitropyrazolo[1,5-a]pyridine 880 g of Oxone (5 eq.), 2 liters of water and 60 g of 2-methylsulfonyl-3-nitropyrazolo[1,5-a]pyridine (0.287 eq.) obtained previously are successively placed in a 4-liter three-necked flask equipped with a mechanical stirrer and an internal temperature probe. The mixture is stirred at room temperature.

To complete the reaction, Oxone (120 g, 0.7 eq.) is added, and, after stirring for 4 hours at room temperature, the reaction is complete.

The solid formed is drained by suction and washed thoroughly with water until a filtrate no longer containing any peroxides is obtained. It is then placed under vacuum at 40° C. over P2O5.

59 g of expected product are obtained in the form of a beige-yellow powder.

The NMR spectrum indicates that the product obtained corresponds to the expected product.

Step 3: Synthesis of N,N-dimethyl-1-(3-nitropyrazolo[1,5-a]pyridin-2-yl)pyrrolidin-3-amine

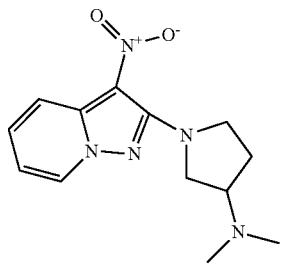 [SMILES: CN(C)C1CCN(c2nn3ccccc3c2[N+](=O)[O-])C1]

5 ml of NMP (N-methylpyrrolidone), 3 g of 2-(methylsulfonyl)-3-nitropyrazolo[1,5-a]pyridine and 3.77 ml of 3-(dimethylamino)pyrrolidine are placed in a 100 ml three-necked flask on which is mounted a bubble condenser, a thermometer and a magnetic stirrer, and the mixture is heated at 80° C. for 1 hour.

After cooling the reaction medium to room temperature, it is poured into a mixture of 200 g of ice and water. The yellow compound that crystallizes out is drained off by suction on a No. 3 sinter and washed with 2×100 ml of water and then with 3×100 ml of isopropyl ether. After drying at 35° C. under vacuum in the presence of P2O5 for 12 hours, 3.26 g of a yellow solid corresponding to the expected compound are recovered.

The NMR (1H 400 MHz and 13C 100.61 MHz DMSO-d6) and mass spectrometry analyses are in accordance with the expected structure.

The quasi-molecular ion (MH)+ of the expected molecule, C13H17N5O2, is mainly detected.

Step 4: Synthesis of N,N,N-trimethyl-1-(3-nitropyrazolo[1,5-a]pyridin-2-yl)pyrrolidin-3-aminium methyl sulfate

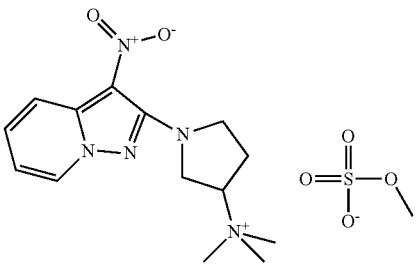

25 ml of THF, 3.26 g (0.01 mol) of N,N-dimethyl-1-(3-nitropyrazolo[1,5-a]pyridin-2-yl)pyrrolidin-3-amine and, dropwise, 1.89 ml (0.02 mol) of dimethyl sulfate are added to a 100 ml three-necked flask on which is mounted a bubble condenser, a thermometer and a magnetic stirrer, at 50° C.

The reaction is monitored by TLC (eluent: 95/5 dichloromethane/methanol).

The medium is cooled to room temperature and the yellow solid formed is drained by suction on a No. 3 sinter and washed with 2×100 ml of THF and then with 3×100 ml of isopropyl ether. After drying at 35° C. under vacuum in the presence of P2O5 for 12 hours, 3.2 g of a yellow solid corresponding to the expected structure are recovered.

The NMR (1H 400 MHz and 13C 100.61 MHz DMSO-d6) and mass spectrometry analyses are in accordance with the expected structure.

Step 5: Synthesis of 1-(3-amino-4,5,6,7-tetrahydropyrazolo[1,5-a]pyridin-2-yl)-N,N,N-trimethylpyrrolidin-3-aminium chloride hydrochloride

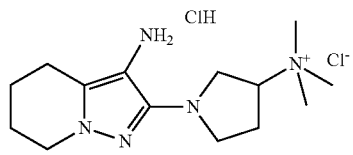 [SMILES: Cl ; C[N+](C)(C)C1CCN(c2nn3c(c2N)CCCC3)C1 ; [Cl-]]

100 ml of ethanol/water (9/1), 1 g (2.56 mmol) of N,N,N-trimethyl-1-(3-nitropyrazolo[1,5-a]pyridin-2-yl)pyrrolidin-3-aminium methyl sulfate and 0.3 g of 50% aqueous 5% palladium are placed in a 300 ml hydrogenator.

The system is purged three times with nitrogen and then once with hydrogen, and the reduction reaction is then performed at a hydrogen pressure of 8 bar, with stirring.

After reaction for 2 hours, the hydrogen consumption falls to zero. After purging several times by flushing with nitrogen, the catalyst is removed by filtration under nitrogen.

The filtrates are acidified with 6N hydrochloric isopropanol and the solvents are evaporated off under vacuum. The residue is taken up in a methanol/petroleum ether mixture, followed by evaporation under vacuum until a brown powder corresponding to the expected compound is obtained.

The NMR analyses ($^1$H 400 MHz and $^{13}$C 100.61 MHz DMSO-$d_6$) are in accordance with the expected structure.

The expected cation, $C_{14}H_{26}N_5^+$, is mainly detected.

Example 2

Synthesis of N,N-dimethyl-N'-(3-nitropyrazolo[1,5-a]pyridin-2-yl)ethane-1,2-diamine methosulfate

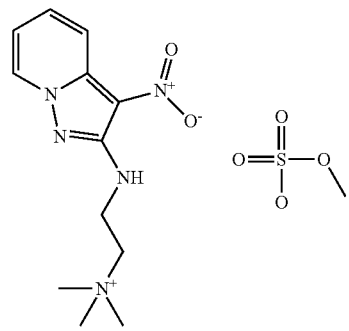

N, N, N-trimethyl-2-[(3-nitropyrazolo[1,5-a]pyridin-2-yl)amino]
ethanaminium methosulfate 35 g (0.140) mol of N,N-dimethyl-N'-(3-nitropyrazolo[1,5-a]pyridin-2-yl)ethane-1,2-diamine are placed in a 500 ml three-necked flask equipped with a bubble condenser, a thermometer and a 50 ml dropping funnel, under magnetic stirring, and containing 200 ml of THF. The temperature is brought to 50° C. using an oil bath, and dimethyl sulfate (1.1 equivalents) is added dropwise; a yellow precipitate forms. The reaction is monitored by TLC (eluent: 98/2 dichloromethane/methanol) until the starting material has disappeared. The solid formed is drained by suction and then washed several times with THF. After drying under vacuum in the presence of $P_2O_5$, 50.8 g of yellow powder are recovered.

The NMR analyses (1H 400 MHz and 13C 100.61 MHz DMSO-d6) are in accordance with the expected structure.

The expected cation, C12H14N5O2+, is mainly detected at m/z=264 in ES+.

Synthesis of [2-(3-aminopyrazolo[1,5-a]pyridin-2-ylamino)ethyl]trimethylammonium chloride dihydrochloride

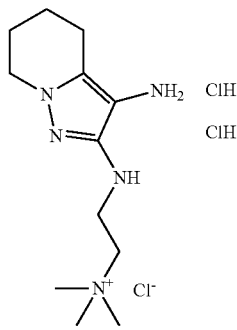 [SMILES: C[N+](C)(C)CCNc1nn2c(c1N)CCCC2 ; [Cl-] ; Cl ; Cl]

150 ml of ethanol, 30 ml of water, 8 g (21.31 mmol) of N,N-dimethyl-N'-(3-nitropyrazolo[1,5-a]pyridin-2-yl) ethane-1,2-diamine methosulfate and 0.8 g of 50% aqueous 5% palladium are placed in a 300 ml hydrogenator.

The system is purged three times with nitrogen and then once with hydrogen, and the reduction reaction is performed at a hydrogen pressure of 8 bar, with stirring.

After reaction for 2 hours, the hydrogen consumption falls to zero. After purging several times by flushing with nitrogen, the catalyst is removed by filtration under nitrogen.

The filtrates are acidified with 6N hydrochloric isopropanol and the solvents are evaporated off under vacuum. The residue is taken up in a methanol/petroleum ether mixture, followed by evaporation under vacuum until a grey powder corresponding to the expected compound is obtained, in a mass of 6 g.

The NMR analyses (1H 400 MHz and 13C 100.61 MHz DMSO-d6) are in accordance with the expected structure.

Analysis by mass spectrometry confirms the product: the expected cation [C12H24N5]+ is mainly detected at m/z ESP+=238.

Example 3

2-(4-Methylpiperazin-1-yl)-3-nitropyrazolo[1,5-a]pyridine

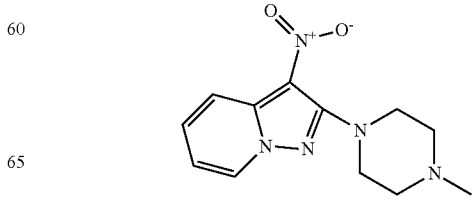

5 ml of NMP, 3 g of 2-(methylsulfonyl)-3-nitropyrazolo[1,5-a]pyridine and 3.3 ml of 1-methylpiperazine are placed in a 100 ml three-necked flask on which is mounted a bubble condenser, a thermometer and a magnetic stirrer, and the mixture is heated at 80° C. for 3 hours.

The medium is poured into a mixture of 200 g of ice and water. The yellow compound that crystallizes out is drained off by suction on a No. 3 sinter and washed with 2×100 ml of water and then with 3×100 ml of isopropyl ether. After drying at 35° C. under vacuum in the presence of P2O5 for 12 hours, 2.35 g of a yellow solid corresponding to the expected compound are recovered.

The NMR ($^1$H 400 MHz and $^{13}$C 100.61 MHz DMSO-$d_6$) and mass spectrometry analyses are in accordance with the expected structure.

The quasi-molecular ions [M+H]+, [M+H+CH3CN]+, [2M+H]+ and the ion of the expected molecule C12H15N5O2 are mainly detected.

Synthesis of 1,1-dimethyl-4-(3-nitropyrazolo[1,5-a]pyridin-2-yl)piperazin-1-ium methyl sulfate

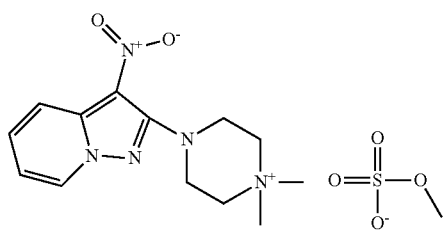

25 ml of THF, 2.35 g (0.01 mol) of 2-(4-methylpiperazin-1-yl)-3-nitropyrazolo[1,5-a]pyridine and, dropwise, 1.85 ml (0.02 mol) of dimethyl sulfate are added to a 100 ml three-necked flask on which is mounted a bubble condenser, a thermometer and a magnetic stirrer, at 50° C.

The reaction is monitored by TLC (eluent: 95/5 dichloromethane/methanol).

The medium is cooled to room temperature and the yellow solid formed is drained by suction on a No. 3 sinter and washed with 2×100 ml of THF and then with 3×100 ml of isopropyl ether. After drying at 35° C. under vacuum in the presence of P2O5 for 12 hours, 3.2 g of a yellow solid corresponding to the expected structure are recovered.

The NMR (1H 400 MHz and 13C 100.61 MHz DMSO-d6) and mass spectrometry analyses are in accordance.

Synthesis of 4-(3-amino-4,5,6,7-tetrahydropyrazolo[1,5-a]pyridin-2-yl)-1,1-dimethylpiperazin-1-ium chloride hydrochloride

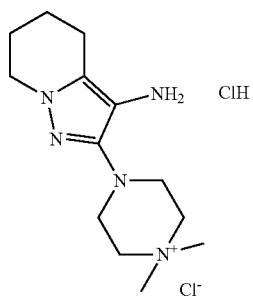 [SMILES: C[N+]1(C)CCN(c2nn3c(c2N)CCCC3)CC1 ; [Cl-] ; Cl]

The compound is obtained according to a procedure identical to that of Example 1, starting with 3 g of 1,1-dimethyl-4-(3-nitropyrazolo[1,5-a]pyridin-2-yl)piperazin-1-ium methyl sulfate.

The filtrates are acidified with 6N hydrochloric isopropanol and the solvents are evaporated off under vacuum. The residue is taken up in a methanol/petroleum ether mixture, followed by evaporation under vacuum to give the expected compound in the form of a beige-coloured powder (mass obtained=1.7 g).

Analysis by mass spectrometry confirms the expected cation [C13H24N5]+.

The NMR analyses (1H 400 MHz and 13C 100.61 MHz DMSO-d6) are in accordance with the expected structure.

Examples of Dyeing

The following dye compositions (A) to (F) are prepared from the ingredients below:

| Compositions | A | B |
|---|---|---|
| 1-(3-amino-4,5,6,7-tetrahydropyrazolo[1,5-a]pyridin-2-yl)-N,N,N-trimethylpyrrolidin-3-aminium chloride hydrochloride | $10^{-3}$ mol | $10^{-3}$ mol |
| 5-amino-2-methylphenol | $10^{-3}$ mol | — |
| 2-(2,4-diaminophenoxy)ethanol hydrochloride | — | $10^{-3}$ mol |
| Dye support (1) | (*) | (*) |
| Demineralized water qs | 100 g | 100 g |
| Shade observed | golden brown | grey |

| Compositions | C | D |
|---|---|---|
| [2-(3-aminopyrazolo[1,5-a]pyridin-2-ylamino)ethyl]trimethylammonium chloride dihydrochloride | $10^{-3}$ mol | $10^{-3}$ mol |
| 5-amino-2-methylphenol | $10^{-3}$ mol | — |
| 2-(2,4-diaminophenoxy)ethanol hydrochloride | — | $10^{-3}$ mol |
| Dye support (1) | (*) | (*) |
| Demineralized water qs | 100 g | 100 g |
| Shade observed | iridescent mahogany red | neutral violet-grey |

| Compositions | E | F |
|---|---|---|
| 4-(3-amino-4, 5, 6, 7-tetrahydropyrazolo [1, 5-a] pyridin-2-yl)-1, 1-dimethylpiperazin-1-ium chloride hydrochloride | $10^{-3}$ mol | $10^{-3}$ mol |
| 5-amino-2-methylphenol | $10^{-3}$ mol | — |
| 2-(2,4-diaminophenoxy)ethanol hydrochloride | — | $10^{-3}$ mol |
| Dye support (1) | (*) | (*) |
| Demineralized water qs | 100 g | 100 g |
| Shade observed | brick red | bluish grey | pH 9.5 Dye Support (1)

| | |
|---|---|
| 96° ethyl alcohol | 20.8 g |
| 35% aqueous sodium metabisulfite solution | 0.23 g AM |

| | |
|---|---|
| pentasodium salt of diethylenetriaminepentaacetic acid as an aqueous 40% solution | 0.48 g AM |
| C$_8$-C$_{10}$ alkyl polyglucoside as an aqueous 60% solution | 3.6 g AM |
| benzyl alcohol | 2.0 g |
| polyethylene glycol containing 8 units of ethylene oxide | 3.0 g |
| NH$_4$Cl | 4.32 g |
| aqueous ammonia containing 20% NH$_3$ | 2.94 g |

At the time of use, each composition is mixed with an equal weight of 20-volumes aqueous hydrogen peroxide solution (6% by weight). A final pH of 9.5 is obtained.

Each mixture obtained is applied to locks of grey hair containing 90% white hairs. After leaving the mixture on for 30 minutes, the locks are rinsed, washed with a standard shampoo, rinsed again and then dried to give the various shades.

The invention claimed is:

1. Cationic tetrahydropyrazolopyridine of formula (I), optical and geometrical isomers thereof, addition salts thereof and/or solvates thereof:

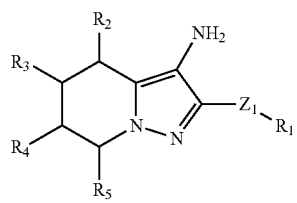

(I)

wherein:
  $R_2$, $R_3$, $R_4$ and $R_5$ represent, independently of each other, a hydrogen atom; a halogen atom; a linear or branched $C_1$-$C_4$ alkyl radical; a linear or branched $C_1$-$C_4$ hydroxyalkyl radical;
  $R_2$ and $R_3$, $R_3$ and $R_4$ or $R_4$ and $R_5$ may form, together with the carbon atoms to which they are attached, a saturated, unsaturated or aromatic 5- to 8-membered ring optionally substituted with one or more radicals chosen from hydroxyl, alkoxy, $C_1$-$C_4$ alkyl and $C_1$-$C_4$ hydroxyalkyl radicals;
  $Z_1$ represents an oxygen atom or a group $NR_6$;
  $R_6$ represents a hydrogen atom or a linear or branched $C_1$-$C_4$ alkyl radical;
  $R_1$ represents:
    a linear or branched $C_1$-$C_{20}$ alkyl radical, substituted and/or interrupted with a cationic radical, the said alkyl radical being optionally interrupted with one or more oxygen atoms and/or with one or more groups NR6, optionally substituted with one or more radicals chosen from hydroxyl and $C_1$-$C_4$ alkoxy or hydroxyalkyl radicals;
    a saturated, unsaturated or aromatic, 5- to 8-membered ring or heterocycle substituted with a cationic radical and optionally substituted with one or more radicals chosen from hydroxyl and $C_1$-$C_4$ alkoxy or hydroxyalkyl radicals;
  when $Z_1$ represents a group $NR_6$ then:
    $R_1$ and $R_6$ may form, together with the nitrogen atom to which they are attached, a saturated, unsaturated, aromatic or non-aromatic, 5- to 8-membered mono- or polycationic, heterocycle, optionally substituted with one or more radicals chosen from $C_1$-$C_4$ alkyl, hydroxyl, $C_1$-$C_4$ alkoxyamino, ($C_1$-$C_4$)alkylamino, ($C_1$-$C_4$)dialkylamino, thio SH, ($C_1$-$C_4$)alkylthio, carboxyl, C(O)OH or C(O)O—, M$^+$ with M+, which may be present or absent depending on the cationic charge number of the compound (I), representing an alkali metal, alkaline-earth metal or ammonium; ($C_1$-$C_4$)alkylcarbonyl; sulfonyl —S(O)$_n$—R, —S(O)$_p$—O—R, —O—S(O)$_p$—R with R representing a hydrogen atom or a $C_1$-$C_4$ (hydroxy)alkyl group, n=0, 1 or 2, p=1 or 2, amido —C(O)—NRR' or —N(R)—C(O)—R', —N(R)—C(O)—NRR' with R and R', which may be identical or different, representing a hydrogen atom or a C1-C4 (hydroxy)alkyl group, C1-C4 hydroxyalkyls, this heterocycle possibly containing one or more heteroatoms chosen from N and O,
    $R_1$ and $R_6$ may form, together with the nitrogen atom to which they are attached, a saturated or unsaturated, 5- to 8-membered noncationic heterocycle optionally substituted with one or more radicals chosen from $C_1$-$C_{10}$ alkyl; hydroxyl; C1-C4 alkoxy; amino; ($C_1$-$C_4$)alkylamino; ($C_1$-$C_4$)dialkylamino; thio SH, ($C_1$-$C_4$)alkylthio, carboxyl, C(O)OH or C(O)O—, M+ with M+, which may be present or absent depending on the cationic charge number of the compound (I), representing an alkali metal, alkaline-earth metal or ammonium; ($C_1$-$C_4$)alkylcarbonyl; sulfonyl —S(O)$_p$—R, —S(O)$_p$—O—R, —O—S(O)$_p$—R with R representing a hydrogen atom or a $C_1$-$C_4$ (hydroxy)alkyl group, n=0, 1 or 2, p=1 or 2, amido —C(O)—NRR' or —N(R)—C(O)—R', —N(R)—C(O)—NRR' with R and R', which may be identical or different, representing a hydrogen atom or a C1-C4 (hydroxy)alkyl group, C1-C4 hydroxyalkyls.

2. Cationic tetrahydropyrazolopyridine of formula (I) according to claim 1, wherein the cationic radical is a linear or branched or heterocyclic radical comprising a quaternary ammonium, this quaternary ammonium being of the type —N$^+$R$_a$R$_b$R$_c$, with R$_a$, R$_b$ and R$_c$, which may be identical or different, representing a $C_1$-$C_6$ alkyl radical which may be substituted with a hydroxyl; R$_a$ and R$_b$ may together form a 5- to 8-membered heterocycle, the radical R$_c$ then being a $C_1$-$C_6$ alkyl radical that may be substituted with a hydroxyl.

3. Cationic tetrahydropyrazolopyridine of formula (I) according to claim 1, wherein, taken together or separately:
  $R_2$, $R_3$, $R_4$ and $R_5$ represent, independently of each other, a hydrogen atom or a linear or branched $C_1$-$C_4$ alkyl radical,
  $R_2$ and $R_3$, $R_3$ and $R_4$ or $R_4$ and $R_5$ may form, together with the carbon atoms that bear them, a saturated, unsaturated or aromatic 5- to 8-membered;
  $Z_1$ represents an oxygen atom or a group $NR_6$;
  $R_6$ represents a hydrogen atom or a linear or branched $C_1$-$C_2$ alkyl radical;
  $R_1$ represents a linear or branched $C_1$-$C_8$ alkyl radical, substituted with a cationic radical, optionally substituted with one or more radicals chosen from $C_1$-$C_4$ alkyl and $C_1$-$C_4$ alkoxy radicals,
  or
  $R_1$ represents a saturated, unsaturated or aromatic, 5- to 8-membered non-cationic ring or heterocycle, substituted with a cationic radical,
  when $Z_1$ represents $NR_6$ then:
    $R_1$ and $R_6$ may form, together with the nitrogen atom to which they are attached, a saturated or unsaturated cationic 5- to 8-membered heterocycle optionally substituted with one or more radicals chosen from C₁-C₁₀ alkyl, hydroxyl, C₁-C₄ alkoxy, amino, (C₁-C₄)alkylamino, di(C₁-C₄)alkylamino, (C₁-C₄)alkylcarbonyl, amido and C₁-C₄ hydroxyalkyl radicals, it being possible for this heterocycle to contain one or more heteroatoms chosen from N or O, or R₁ and R₆ may form, together with the nitrogen atom to which they are attached, a saturated or unsaturated non-cationic 5- to 8-membered heterocycle substituted with a cationic radical and optionally substituted with one or more radicals chosen from C₁-C₁₀ alkyl, hydroxyl, C₁-C₄ alkoxy, amino, (C₁-C₄)alkylamino, di(C₁-C₄)alkylamino, (C₁-C₄)alkylcarbonyl, amido and C₁-C₄ hydroxyalkyl radicals.

4. Cationic tetrahydropyrazolopyridine of formula (I) according to claim 1, wherein the cationic radical is chosen from trimethylammonium, triethylammonium, dimethylethylammonium, diethylmethylammonium, diisopropylmethylammonium, diethylpropylammonium, hydroxyethyldiethylammonium, di-β-hydroxyethylmethylammonium and tri-β-hydroxyethylammonium radicals.

5. Cationic tetrahydropyrazolopyridine of formula (I) according to claim 1, wherein the cationic heterocycle is chosen from imidazoliums, pyridiniums, piperaziniums, pyrrolidiniums, morpholiniums, pyrimidiniums, thiazoliums, benzimidazoliums, benzothiazoliums, oxazoliums, benzotriazoliums, pyrazoliums.

6. Cationic tetrahydropyrazolopyridine of formula (I) according to claim 1, wherein R₂, R₃, R₄ and R₅ represent a hydrogen atom saturated linear C₂-C₈ alkyl radical, optionally interrupted with a heteroatom or a group NH, R₁ being substituted with a cationic radical chosen from trimethylammonium radicals and imidazolium, piperazinium, pyrrolidinium, piperidinium or morpholinium cationic heterocycles.

7. Cationic tetrahydropyrazolopyridine of formula (I) according to claim 1, wherein R₂, R₃, R₄ and R₅ represent a hydrogen atom, Z₁ represents a group NR₆ and R₁ and R₆ form, together with the nitrogen atom to which they are attached, a saturated or unsaturated, 5- to 8-membered non-cationic heterocycle, substituted with a cationic radical.

8. Cationic tetrahydropyrazolopyridine of formula (I) according to claim 1, wherein R₂, R₃, R₄ and R₅ represent a hydrogen atom, Z₁ represents a group NR₆ and R₁ and R₆ form, together with the nitrogen atom to which they are attached, a cationic heterocycle chosen from piperazinium, imidazolium, pyrrolidinium, piperidinium and morpholinium substituted with one or more identical or different radicals chosen from C₁-C₄ hydroxyalkyl and C₁-C₄ alkyl.

9. Cationic tetrahydropyrazolopyridine of formula (I) according to claim 1, wherein the compound is chosen from the following compounds and the geometrical or optical isomer forms thereof, the organic or mineral acid salts thereof or the solvates thereof, Z₁ represents a group NH and R₁ represents a Compound 1

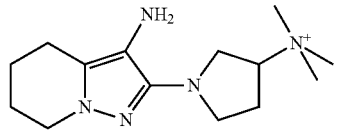

1-(3-amino-4,5,6,7-tetrahydropyrazolo[1,5-a]pyridin-2-yl)-N,N,N-trimethylpyrrolidin-3-aminium, An⁻

-continued

Compound 2

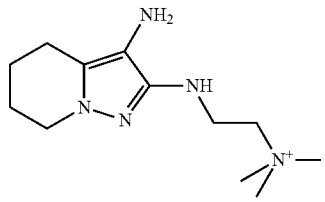

2-[(3-amino-4,5,6,7-tetrahydropyrazolo[1,5-a]pyridin-2-yl)amino]-N,N,N-trimethylethanaminium, An⁻

Compound 3

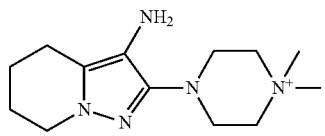

1-(3-amino-4,5,6,7-tetrahydropyrazolo[1,5-a]pyridin-2-yl)-N,N,N-trimethylpyrrolidin-3-aminium, An⁻

Compound 4

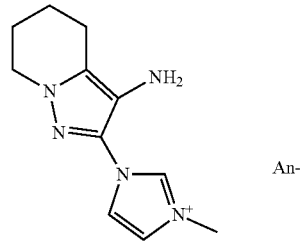

1-(3-amino-4,5,6,7-tetrahydropyrazolo[1,5-a]pyridin-2-yl)-3-methyl-1H-imidazol-3-ium, An⁻

Compound 5

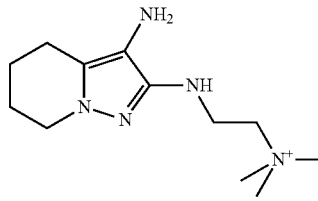

2-[(3-amino-4,5,6,7-tetrahydropyrazolo[1,5-a]pyridin-2-yl)amino]-N-ethyl-N,N-dimethylethanaminium, An⁻

Compound 6

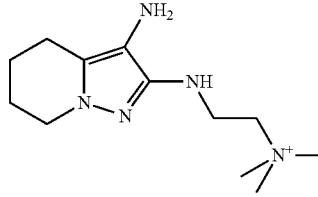

2-[(3-amino-4,5,6,7-tetrahydropyrazolo[1,5-a]pyridin-2-yl)amino]-N-(2-hydroxyethyl)-N,N-dimethylethanaminium, An⁻

Compound 7

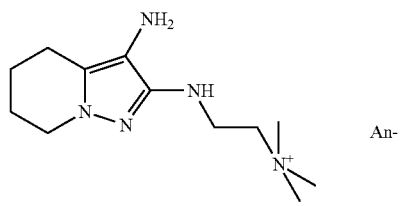

3-[(3-amino-4,5,6,7-tetrahydropyrazolo[1,5-a]pyridin-2-yl)
amino]-N,N,N-trimethylpropan-1-aminium, An⁻

Compound 8

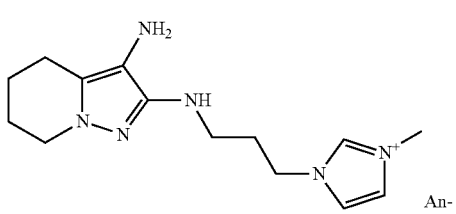

1-{3-[(3-amino-4,5,6,7-tetrahydropyrazolo[1,5-a]pyridin-
2-yl)amino]propyl}-3-methyl-1H-imidazol-3-ium, An⁻

Compound 9

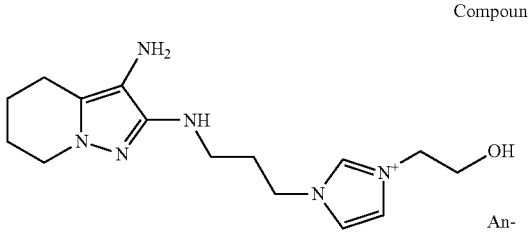

1-{3-[(3-amino-4,5,6,7-tetrahydropyrazolo[1,5-a]pyridin-2-yl)
amino]propyl}-3-(2-hydroxyethyl)-1H-imidazol-3-ium, An⁻

Compound 10

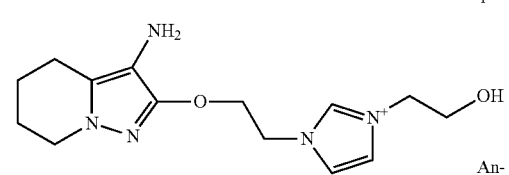

1-{3-[(3-amino-4,5,6,7-tetrahydropyrazolo[1,5-a]pyridin-2-yl)
amino]propyl}-3-(2-hydroxyethyl)-1H-imidazol-3-ium, An⁻

Compound 11

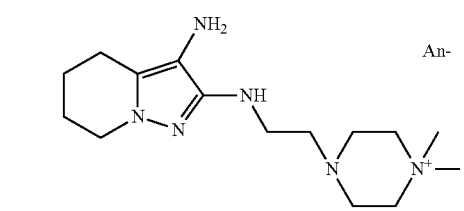

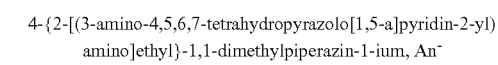

4-{2-[(3-amino-4,5,6,7-tetrahydropyrazolo[1,5-a]pyridin-2-yl)
amino]ethyl}-1,1-dimethylpiperazin-1-ium, An⁻

Compound 12

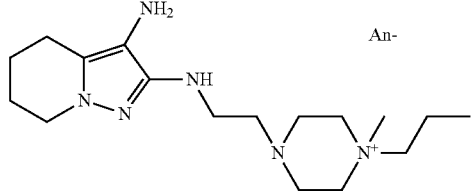

4-{2-[(3-amino-4,5,6,7-tetrahydropyrazolo[1,5-a]pyridin-2-yl)
amino]ethyl}-1-methyl-1-propylpiperazin-1-ium, An⁻

Compound 13

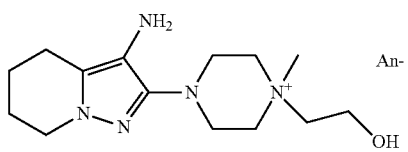

4-(3-amino-4,5,6,7-tetrahydropyrazolo[1,5-a]pyridin-2-yl)-
1-(2-hydroxyethyl)-1-methylpiperazin-1-ium, An⁻

Compound 14

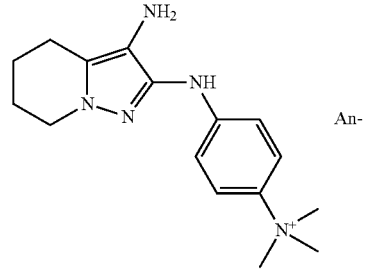

4-[(3-amino-4,5,6,7-tetrahydropyrazolo[1,5-a]
pyridin-2-yl)-amino]-N,N,N-trimethylanilinium, An⁻

Compound 15

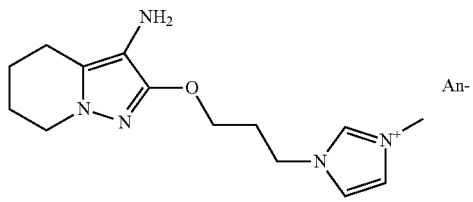

1-{3-[(3-amino-4,5,6,7-tetrahydropyrazolo[1,5-a]pyridin-
2-yl)oxy]propyl}-3-methyl-1H-imidazol-3-ium, An⁻

Compound 16

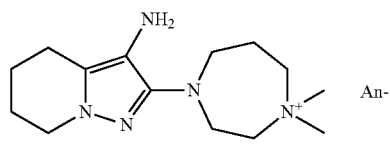

4-(3-amino-4,5,6,7-tetrahydropyrazolo[1,5-a]
pyridin-2-yl)-1,1-dimethyl-1,4-diazepan-1-ium An⁻

Compound 17

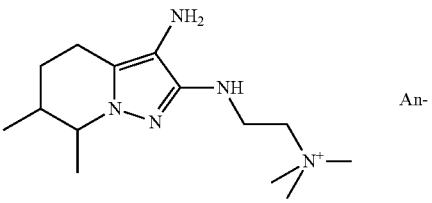

2-[(3-amino-6,7-dimethyl-4,5-dihydropyrazolo[1,5-a]
pyridin-2-yl)amino]-N,N,N-trimethylethanaminium, An⁻

Compound 18

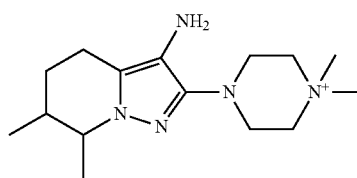

4-(3-amino-6,7-dimethyl-4,5,6,7-tetrahydropyrazolo
[1,5-a]pyridin-2-yl)-1,1-dimethylpiperazin-1-ium, An⁻

Compound 19

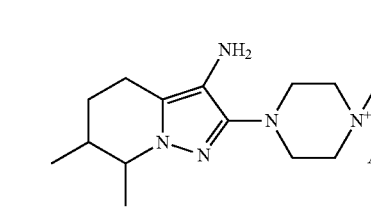

4-(3-amino-6,7-dimethyl-4,5,6,7-tetrahydropyrazolo[1,5-a]
pyridin-2-yl)-1-(2-hydroxyethyl)-1-methylpiperazin-1-ium, An⁻

Compound 20

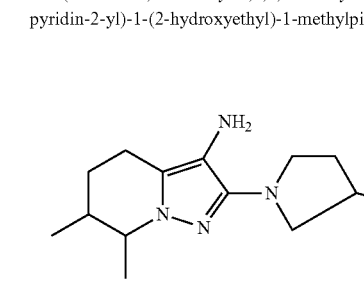

1-(3-amino-6,7-dimethyl-4,5,6,7-tetrahydropyrazolo[1,5-a]
pyridin-2-yl)-N,N,N-trimethylpyrrolidin-3-aminium, An⁻

Compound 21

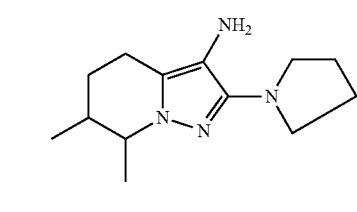

1-(3-amino-6,7-dimethyl-4,5,6,7-tetrahydropyrazolo[1,5-
a]pyridin-2-yl)-N-(2-hydroxyethyl)-N,N-
dimethylpyrrolidin-3-aminium, An⁻

Compound 22

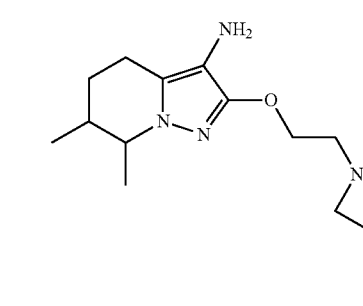

1-{2-[(3-amino-6,7-dimethyl-4,5,6,7-tetrahydropyrazolo[1,5-a]
pyridin-2-yl)oxy]ethyl}-N,N,N-trimethylpyrrolidin-3-aminium, An⁻

Compound 23

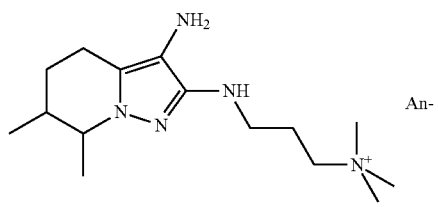

3-[(3-amino-6,7-dimethyl-4,5,6,7-tetrahydropyrazolo[1,5-a]
pyridin-2-yl)amino]-N,N,N-trimethylpropan-1-aminium, An⁻

Compound 24

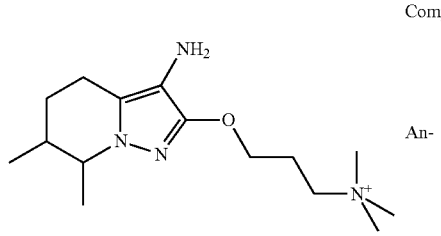

3-[(3-amino-6,7-dimethyl-4,5,6,7-tetrahydropyrazolo[1,5-a]
pyridin-2-yl)oxy]-N,N,N-trimethylpropan-1-aminium, An⁻

Compound 25

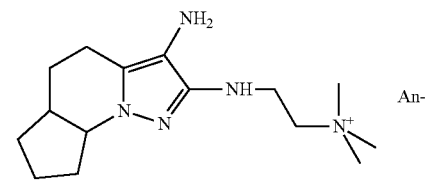

2-[(3-amino-6,7,8,8a-tetrahydro-5aH-cyclopenta[e]pyrazolo
[1,5-a]pyridin-2-yl)amino]-N,N,N-trimethylethanaminium, An⁻

Compound 26

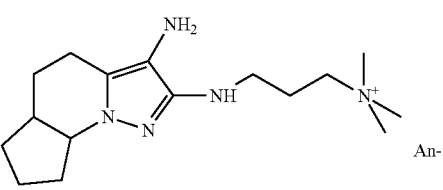

3-[(3-amino-5,5a,6,7,8,8a-hexahydro-4H-cyclopenta[e]pyrazolo
[1,5-a]pyridin-2-yl)amino]-N,N,N-trimethylpropan-1-aminium, An⁻

Compound 27

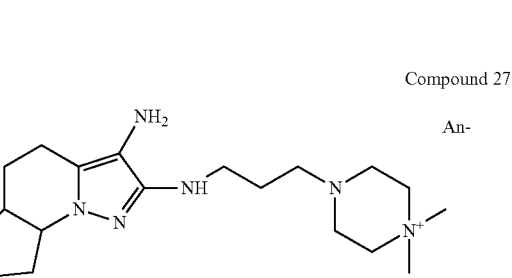

4-{3-[(3-amino-5,5a,6,7,8,8a-hexahydro-4H-cyclopenta[e]pyrazolo
[1,5-a]pyridin-2-yl)amino]propyl}-1,1-dimethylpiperazin-1-ium, An⁻

39
-continued

Compound 28

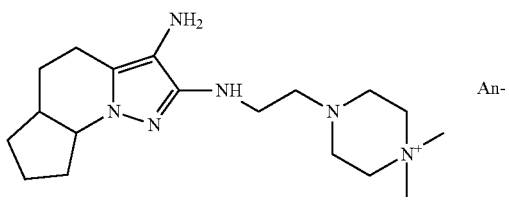

4-{2-[(3-amino-5,5a,6,7,8,8a-hexahydro-4H-cyclopenta[e]pyrazolo
[1,5-a]pyridin-2-yl)amino]ethyl}-1,1-dimethylpiperazin-1-ium, An⁻

Compound 29

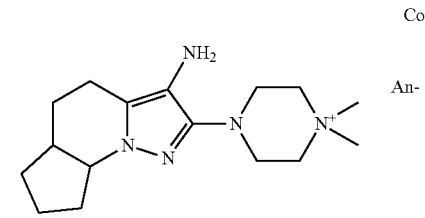

4-[(3-amino-5,5a,6,7,8,8a-hexahydro-4H-cyclopenta[e]pyrazolo
[1,5-a]pyridin-2-yl)-1,1-dimethylpiperazin-1-ium, An⁻

Compound 30

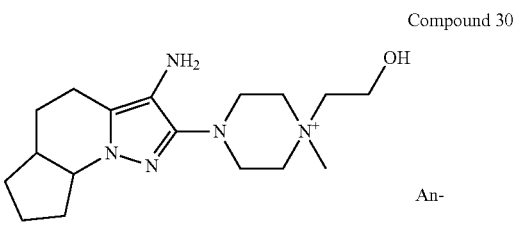

4-[(3-amino-5,5a,6,7,8,8a-hexahydro-4H-cyclopenta[e]pyrazolo
[1,5-a]pyridin-2-yl)-1-(2-hydroxyethyl)-1-methylpiperazin-1-ium, An⁻

Compound 31

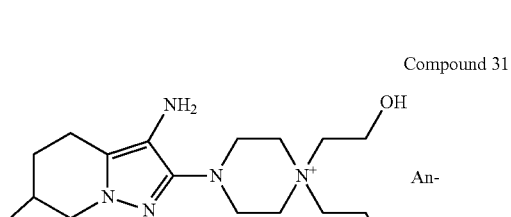

4-[(3-amino-5,5a,6,7,8,8a-hexahydro-4H-cyclopenta[e]pyrazolo
[1,5-a]pyridin-2-yl)-1,1-bis(2-hydroxyethyl)piperazin-1-ium, An⁻

Compound 32

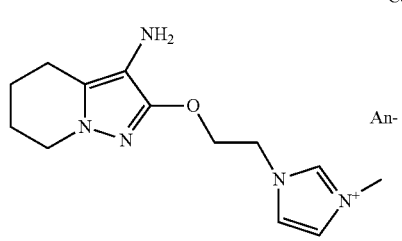

1-{2-[(3-amino-4,5,6,7-tetrahydropyrazolo[1,5-a]pyridin-
2-yl)oxy]ethyl}-3-methyl-1H-imidazol-3-ium, An⁻

40
-continued

Compound 33

2-[(3-amino-4,5,6,7-tetrahydropyrazolo[1,5-a]pyridin-
2-yl)oxy]-N,N,N-trimethylethanaminium, An⁻

Compound 34

1-{2-[(3-amino-4,5,6,7-tetrahydropyrazolo[1,5-a]pyridin-
2-yl)oxy]ethyl}-N,N,N-trimethylpyrrolidin-3-aminium, An⁻

Compound 35

4-{2-[(3-amino-5,5a,6,7,8,8a-hexahydro-4H-cyclopenta[e]pyrazolo
[1,5-a]pyridin-2-yl)oxy]ethyl}-1,1-dimethylpiperazin-1-ium, An⁻

10. A process for synthesizing a cationic tetrahydropyrazolopyridine of general formula (I):

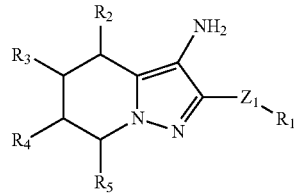

(I)

wherein:
$R_2$, $R_3$, $R_4$ and $R_5$ represent, independently of each other, a hydrogen atom; a halogen atom; a linear or branched $C_1$-$C_4$ alkyl radical; a linear or branched $C_1$-$C_4$ hydroxyalkyl radical;

$R_2$ and $R_3$, $R_3$ and $R_4$ or $R_4$ and $R_5$ may form, together with the carbon atoms to which they are attached, a saturated, unsaturated or aromatic 5- to 8-membered ring optionally substituted with one or more radicals chosen from hydroxyl, alkoxy, $C_1$-$C_4$ alkyl and $C_1$-$C_4$ hydroxyalkyl radicals;

$Z_1$ represents an oxygen atom or a group $NR_6$;
$R_6$ represents a hydrogen atom or a linear or branched $C_1$-$C_4$ alkyl radical;

$R_1$ represents:

a linear or branched $C_1$-$C_{20}$ alkyl radical, substituted and/or interrupted with a cationic radical, the said alkyl radical being optionally interrupted with one or more oxygen atoms and/or with one or more groups NR6, optionally substituted with one or more radicals chosen from hydroxyl and $C_1$-$C_4$ alkoxy or hydroxyalkyl radicals;

a saturated, unsaturated or aromatic, 5- to 8-membered ring or heterocycle substituted with a cationic radical and optionally substituted with one or more radicals chosen from hydroxyl and $C_1$-$C_4$ alkoxy or hydroxyalkyl radicals;

when $Z_1$ represents a group $NR_6$ then:

$R_1$ and $R_6$ may form, together with the nitrogen atom to which they are attached, a saturated, unsaturated, aromatic or non-aromatic, 5- to 8-membered mono- or polycationic, heterocycle, optionally substituted with one or more radicals chosen from $C_1$-$C_4$ alkyl, hydroxyl, $C_1$-$C_4$ alkoxyamino, ($C_1$-$C_4$)alkylamino, ($C_1$-$C_4$)dialkylamino, thio SH, ($C_1$-$C_4$)alkylthio, carboxyl, C(O)OH or C(O)O—, M+ with M+, which may be present or absent depending on the cationic charge number of the compound (I), representing an alkali metal, alkaline-earth metal or ammonium; ($C_1$-$C_4$) alkylcarbonyl; sulfonyl —S(O)$_p$—R, —S(O)$_p$—O—R, —O—S(O)$_p$—R with R representing a hydrogen atom or a $C_1$-$C_4$ (hydroxy)alkyl group, n=0, 1 or 2, p=1 or 2, amido —C(O)—NRR' or —N(R)—C(O)—R', —N(R)—C(O)—NRR' with R and R', which may be identical or different, representing a hydrogen atom or a C1-C4 (hydroxy)alkyl group, C1-C4 hydroxyalkyls, this heterocycle possibly containing one or more heteroatoms chosen from N and O, $R_1$ and $R_6$ may form, together with the nitrogen atom to which they are attached, a saturated or unsaturated, 5- to 8-membered noncationic heterocycle optionally substituted with one or more radicals chosen from $C_1$-$C_{10}$ alkyl; hydroxyl; C1-C4 alkoxy; amino; ($C_1$-$C_4$)alkylamino; ($C_1$-$C_4$)dialkylamino; thio SH, ($C_1$-$C_4$)alkylthio, carboxyl, C(O)OH or C(O)O—, M+ with M+, which may be present or absent depending on the cationic charge number of the compound (I), representing an alkali metal, alkaline-earth metal or ammonium; ($C_1$-$C_4$) alkylcarbonyl; sulfonyl —S(O)$_n$—R, —S(O)$_p$—O—R, —O—S(O)$_p$—R with R representing a hydrogen atom or a $C_1$-$C_4$ (hydroxy)alkyl group, n=0, 1 or 2, p=1 or 2, amido —C(O)—NRR' or —N(R)—C(O)—R', —N(R)—C(O)—NRR' with R and R', which may be identical or different, representing a hydrogen atom or a C1-C4 (hydroxy)alkyl group, C1-C4 hydroxyalkyls;

starting with compounds (A), (B), (C) and (D) according to the following scheme:

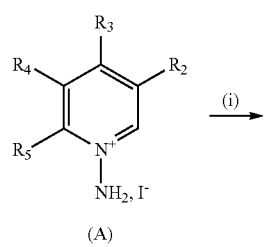

(A)

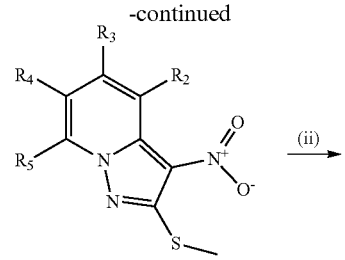

(B)

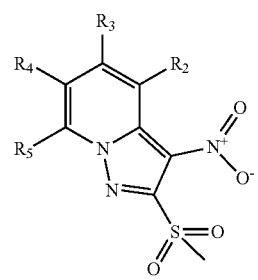

(C)

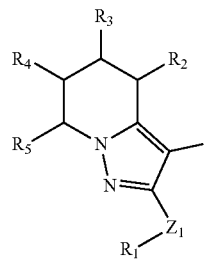

(I)

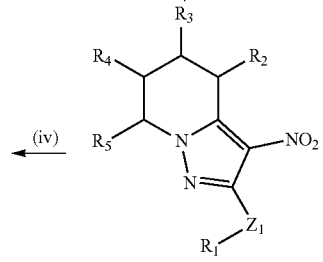

(D)

wherein $R_1$, $Z_1$, $R_2$, $R_3$, $R_4$ and $R_5$ have the same meanings as those indicated in formula (I), and wherein:

in a step (i), an N-aminopyridinium derivative of formula (A) is reacted with at least two equivalents of 1,1-bis(methylthio)-2-nitroethylene, to obtain a 2-methylsulfanyl-3-nitropyrazolo[1,5-a]pyridine derivative of formula (B), in a step (ii), an oxidation reaction is performed on the compound of formula (B) to obtain an N,N-dimethyl-1-(3-nitropyrazolo[1,5-a]pyridin-2-yl)pyrrolidin-3-amine derivative of formula (C), in a step (iii), the compound of formula (C) is reacted with a compound of formula $R_1Z_1H$ or $R_1Z_1^-$, M+ with M+ representing an alkali metal or an alkaline-earth metal such as Li, Na or K, in order to replace the group —S(O)$_2$—CH$_3$ with a group —Z$_1$R$_1$ in order to obtain the compound of formula (D), and in a step (iv), one or more reduction reactions are performed, on the compound of formula (D) to give a cationic tetrahydropyrazolopyridine of formula (I).

11. Compounds of formula (D) according to claim 10.

12. Composition for dyeing keratin fibers, comprising, in a suitable dyeing medium, one or more cationic tetrahydropyrazolopyridines of formula (I):

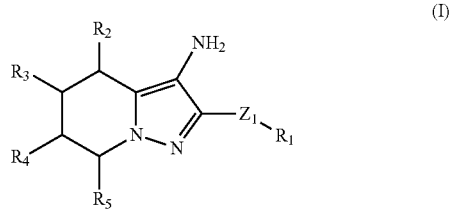

(I)

wherein:
- $R_2$, $R_3$, $R_4$ and $R_5$ represent, independently of each other, a hydrogen atom; a halogen atom; a linear or branched $C_1$-$C_4$ alkyl radical; a linear or branched $C_1$-$C_4$ hydroxyalkyl radical;
- $R_2$ and $R_3$, $R_3$ and $R_4$ or $R_4$ and $R_5$ may form, together with the carbon atoms to which they are attached, a saturated, unsaturated or aromatic 5- to 8-membered ring optionally substituted with one or more radicals chosen from hydroxyl, alkoxy, $C_1$-$C_4$ alkyl and $C_1$-$C_4$ hydroxyalkyl radicals;
- $Z_1$ represents an oxygen atom or a group $NR_6$;
- $R_6$ represents a hydrogen atom or a linear or branched $C_1$-$C_4$ alkyl radical;
- $R_1$ represents:
  - a linear or branched $C_1$-$C_{20}$ alkyl radical, substituted and/or interrupted with a cationic radical, the said alkyl radical being optionally interrupted with one or more oxygen atoms and/or with one or more groups NR6, optionally substituted with one or more radicals chosen from hydroxyl and $C_1$-$C_4$ alkoxy or hydroxyalkyl radicals;
  - a saturated, unsaturated or aromatic, 5- to 8-membered ring or heterocycle substituted with a cationic radical and optionally substituted with one or more radicals chosen from hydroxyl and $C_1$-$C_4$ alkoxy or hydroxyalkyl radicals;
- when $Z_1$ represents a group $NR_6$ then:
  - $R_1$ and $R_6$ may form, together with the nitrogen atom to which they are attached, a saturated, unsaturated, aromatic or non-aromatic, 5- to 8-membered mono- or polycationic, heterocycle, optionally substituted with one or more radicals chosen from $C_1$-$C_4$ alkyl, hydroxyl, $C_1$-$C_4$ alkoxyamino, ($C_1$-$C_4$)alkylamino, ($C_1$-$C_4$)dialkylamino, thio SH, ($C_1$-$C_4$)alkylthio, carboxyl, C(O)OH or C(O)O—, $M^+$ with $M^+$, which may be present or absent depending on the cationic charge number of the compound (I), representing an alkali metal, alkaline-earth metal or ammonium; ($C_1$-$C_4$) alkylcarbonyl; sulfonyl —S(O)$_n$—R, —S(O)$_p$—O—R, —O—S(O)$_p$—R with R representing a hydrogen atom or a $C_1$-$C_4$ (hydroxy)alkyl group, n=0, 1 or 2, p=1 or 2, amido —C(O)—NRR' or —N(R)—C(O)—R', —N(R)—C(O)—NRR' with R and R', which may be identical or different, representing a hydrogen atom or a C1-C4 (hydroxy)alkyl group, C1-C4 hydroxyalkyls, this heterocycle possibly containing one or more heteroatoms chosen from N and O,
  - $R_1$ and $R_6$ may form, together with the nitrogen atom to which they are attached, a saturated or unsaturated, 5- to 8-membered noncationic heterocycle optionally substituted with one or more radicals chosen from $C_1$-$C_{10}$ alkyl; hydroxyl; C1-C4 alkoxy; amino; ($C_1$-$C_4$)alkylamino; ($C_1$-$C_4$)dialkylamino; thio SH, ($C_1$-$C_4$)alkylthio, carboxyl, C(O)OH or C(O)O—, M+ with M+, which may be present or absent depending on the cationic charge number of the compound (I), representing an alkali metal, alkaline-earth metal or ammonium; ($C_1$-$C_4$)alkylcarbonyl; sulfonyl —S(O)$_n$—R, —S(O)$_p$—O—R, —O—S(O)$_p$—R with R representing a hydrogen atom or a $C_1$-$C_4$ (hydroxy)alkyl group, n=0, 1 or 2, p=1 or 2, amido —C(O)—NRR' or —N(R)—C(O)—R', —N(R)—C(O)—NRR' with R and R', which may be identical or different, representing a hydrogen atom or a C1-C4 (hydroxy)alkyl group, C1-C4 hydroxyalkyls.

13. Process for dyeing keratin fibers, the process comprising:
applying to the said fibers in the presence of one or more oxidizing agents, and optionally one or more couplers, for a time that is sufficient to obtain a desired coloration, a dye composition comprising a cationic tetrahydropyrazolopyridine of formula (I):

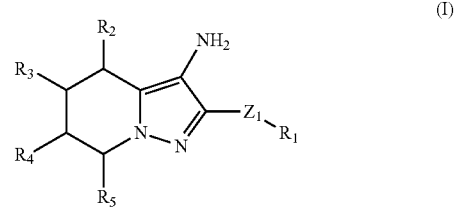

(I)

wherein:
- $R_2$, $R_3$, $R_4$ and $R_5$ represent, independently of each other, a hydrogen atom; a halogen atom; a linear or branched $C_1$-$C_4$ alkyl radical; a linear or branched $C_1$-$C_4$ hydroxyalkyl radical;
- $R_2$ and $R_3$, $R_3$ and $R_4$ or $R_4$ and $R_5$ may form, together with the carbon atoms to which they are attached, a saturated, unsaturated or aromatic 5- to 8-membered ring optionally substituted with one or more radicals chosen from hydroxyl, alkoxy, $C_1$-$C_4$ alkyl and $C_1$-$C_4$ hydroxyalkyl radicals;
- $Z_1$ represents an oxygen atom or a group $NR_6$;
- $R_6$ represents a hydrogen atom or a linear or branched $C_1$-$C_4$ alkyl radical;
- $R_1$ represents:
  - a linear or branched $C_1$-$C_{20}$ alkyl radical, substituted and/or interrupted with a cationic radical, the said alkyl radical being optionally interrupted with one or more oxygen atoms and/or with one or more groups NR6, optionally substituted with one or more radicals chosen from hydroxyl and $C_1$-$C_4$ alkoxy or hydroxyalkyl radicals;
  - a saturated, unsaturated or aromatic, 5- to 8-membered ring or heterocycle substituted with a cationic radical and optionally substituted with one or more radicals chosen from hydroxyl and $C_1$-$C_4$ alkoxy or hydroxyalkyl radicals;
- when $Z_1$ represents a group $NR_6$ then:
  - $R_1$ and $R_6$ may form, together with the nitrogen atom to which they are attached, a saturated, unsaturated, aromatic or non-aromatic, 5- to 8-membered mono- or polycationic, heterocycle, optionally substituted with one or more radicals chosen from $C_1$-$C_4$ alkyl, hydroxyl, $C_1$-$C_4$ alkoxyamino, ($C_1$-$C_4$)alkylamino, ($C_1$-$C_4$)dialkylamino, thio SH, ($C_1$-$C_4$)alkylthio, carboxyl, C(O)OH or C(O)O—, $M^+$ with $M^+$, which may be present or absent depending on the cationic charge number of the compound (I), representing an alkali metal, alkaline-earth metal or ammonium; $(C_1-C_4)$ alkylcarbonyl; sulfonyl —S(O)$_n$—R, —S(O)$_p$—O—R, —O—S(O)$_p$—R with R representing a hydrogen atom or a $C_1$-$C_4$ (hydroxy)alkyl group, n=0, 1 or 2, p=1 or 2, amido —C(O)—NRR' or —N(R)—C(O)—R', —N(R)—C(O)—NRR' with R and R', which may be identical or different, representing a hydrogen atom or a C1-C4 (hydroxy)alkyl group, C1-C4 hydroxyalkyls, this heterocycle possibly containing one or more heteroatoms chosen from N and O, $R_1$ and $R_6$ may form, together with the nitrogen atom to which they are attached, a saturated or unsaturated, 5- to 8-membered noncationic heterocycle optionally substituted with one or more radicals chosen from $C_1$-$C_{10}$ alkyl; hydroxyl; C1-C4 alkoxy; amino; $(C_1$-$C_4)$alkylamino; $(C_1$-$C_4)$dialkylamino; thio SH, $(C_1$-$C_4)$alkylthio, carboxyl, C(O)OH or C(O)O—, M+ with M+, which may be present or absent depending on the cationic charge number of the compound (I), representing an alkali metal, alkaline-earth metal or ammonium; $(C_1$-$C_4)$alkylcarbonyl; sulfonyl —S(O)$_n$—R, —S(O)$_p$—O—R, —O—S(O)$_p$—R with R representing a hydrogen atom or a C1-C4 (hydroxy)alkyl group, n=0, 1 or 2, p=1 or 2, amido —C(O)—NRR' or —N(R)—C(O)—R', —N(R)—C(O)—NRR' with R and R', which may be identical or different, representing a hydrogen atom or a C1-C4 (hydroxy)alkyl group, C1-C4 hydroxyalkyls;

rinsing the resulting fibers;

optionally washing the fibers with shampoo, optionally rinsing the fibers again; and drying the fibers or leaving the fibers to dry.

14. Multi-compartment device or dyeing kit, comprising a first compartment configured to contain a dye composition according to claim 12, and a second compartment configured to contain at least one oxidizing agents.

15. Cationic tetrahydropyrazolopyridine of formula (I) according to claim 1, wherein the cationic heterocycle is chosen from pyrrolidine, piperidine, morpholine and piperazine rings, triazolliums and benzoxazoliums.

\* \* \* \* \*

UNITED STATES PATENT AND TRADEMARK OFFICE
CERTIFICATE OF CORRECTION

Page 1 of 1

PATENT NO.       : 9,078,828 B2
APPLICATION NO.  : 14/365710
DATED            : July 14, 2015
INVENTOR(S)      : Aziz Fadli It is certified that error appears in the above-identified patent and that said Letters Patent is hereby corrected as shown below:

In the claims

Claim 1, col. 32, line 29, please change "--S(O)p--R," to -- --S(O)n--R, --.

Claim 10, col. 41, line 29, please change "--S(O)p--R," to -- --S(O)n--R, --.

Signed and Sealed this
Twelfth Day of January, 2016

Michelle K. Lee
*Director of the United States Patent and Trademark Office*